United States Patent
Schraermeyer et al.

(10) Patent No.: US 10,495,630 B2
(45) Date of Patent: Dec. 3, 2019

(54) METHODS FOR THE DETERMINATION OF COMPOUNDS OR COMPOSITIONS FOR THE TREATMENT OF LIPOFUSCIN RELATED DISEASES AND COMPOUNDS OR COMPOSITIONS

(71) Applicant: KATAIRO GMBH, Kusterdingen (DE)

(72) Inventors: Ulrich Schraermeyer, Hechingen (DE); Michael Burnet, Tuebingen (DE); Jörg Senn-Bilfinger, Constance (DE); Ernst Sturm, Constance (DE); Guido Hanauer, Constance (DE)

(73) Assignees: KATAIRO GMBH, Kusterdingen (DE); TAKEDA GMBH, Constance (DE)

( * ) Notice: Subject to any disclaimer, the term of this patent is extended or adjusted under 35 U.S.C. 154(b) by 34 days.

(21) Appl. No.: 15/118,486

(22) PCT Filed: Feb. 13, 2015

(86) PCT No.: PCT/EP2015/053148
§ 371 (c)(1),
(2) Date: Aug. 12, 2016

(87) PCT Pub. No.: WO2015/121441
PCT Pub. Date: Aug. 20, 2015

(65) Prior Publication Data
US 2017/0176416 A1    Jun. 22, 2017

(30) Foreign Application Priority Data
Feb. 13, 2014    (EP) .................................... 14155057

(51) Int. Cl.
*C12Q 1/02*     (2006.01)
*G01N 33/50*   (2006.01)
*G01N 33/92*   (2006.01)

(52) U.S. Cl.
CPC ......... *G01N 33/5044* (2013.01); *G01N 33/92* (2013.01); *G01N 2500/04* (2013.01); *G01N 2800/164* (2013.01)

(58) Field of Classification Search
CPC ...................................................... C12Q 1/025
See application file for complete search history.

(56) References Cited

U.S. PATENT DOCUMENTS

2008/0254140 A1    10/2008    Widder et al.
2011/0034554 A1    2/2011    Washingon
(Continued)

FOREIGN PATENT DOCUMENTS

EP    2 080 513 A1    7/2009
WO    WO 2006/033734 A2    3/2006
(Continued)

OTHER PUBLICATIONS

L. J. Scott et al.: "Verteporfin", Drugs & Aging, vol. 16, No. 2, pp. 139-146 (2000).
(Continued)

*Primary Examiner* — Rosanne Kosson
(74) *Attorney, Agent, or Firm* — Sughrue Mion, PLLC

(57) ABSTRACT

A method for selecting a compound or a composition suitable for treating lipofuscin associated diseases in a patient, the method including the steps of determining a reactivity factor, determining a targeting factor that allows an uptake into a cell and a provides a targeting of lipofuscin, and selecting a compound or a composition or combining compounds to obtain a compound or composition that comprises a reactivity factor and an targeting factor.

9 Claims, 9 Drawing Sheets

(56) References Cited

U.S. PATENT DOCUMENTS

| | | |
|---|---|---|
| 2011/0046377 A1 | 2/2011 | Schaermeyer |
| 2015/0126494 A1 | 5/2015 | Petrukhin et al. |

FOREIGN PATENT DOCUMENTS

| | | |
|---|---|---|
| WO | WO 2007/008821 A2 | 1/2007 |
| WO | WO 2009/035673 A1 | 3/2009 |
| WO | WO 2013/166037 A1 | 11/2013 |

OTHER PUBLICATIONS

Anonymus: "Visudyne® (verteporfin for injection) Prescribing Information", Valeant Ophthalmics, Novartis, p. 4924 (2014).
Y. Wu et al.: "Enzymatic Degradation of A2E, a Retinal Pigment Epithelial Lipofuscin Bisretinoid", Journal of the American Chemical Society, vol. 133, pp. 849-857 (2011).
R. A. Radu et al.: "Treatment with isotretinoin inhibits lipofuscin accumulation in a mouse model of recessive Stargardt's macular degeneration", PNAS, vol. 100, No. 8, pp. 4742-4747 (2003).
C. J. Kennedy et al.: "Lipofuscin of the Retinal Pigment Epithelium: A Review", Eye, vol. 9, pp. 763-771 (1995).
A. Terman et al.: "Lipofuscin: Mechanisms of formation and increase with age", APMIS, vol. 106, pp. 265-276 (1998).
G. Giaccone et al.: "Lipofuscin Hypothesis of Alzheimer's Disease", Dementia and Geriatric Cognitive Disorders, vol. 1, pp. 292-296 (2011).
A. Höhn et al.: "Lipofuscin: formation, effects and role of macroautophagy", Redox Biology, vol. 1, pp. 140-144 (2013).
S. Julien et al.: "Lipofuscin can be eliminated from the retinal pigment epithelium of monkeys", Neurobiology of Aging, vol. 33, pp. 2390-2397 (2012).
S. Julien et al.: "Lipofuscin Can Be Eliminated From Retinal Pigment Epithelium After Drug Treatment", ARVO Meeting Abstracts, vol. 51, p. 481 (2010).
T. Hasan et al.: "Mechanism of Tetracycline Phototoxicity", The Journal of Investigative Dermatology, vol. 83, pp. 179-183 (1984).
L. J. Martinez et al.: "Fluoroquinolone Antimicrobials: Singlet Oxygen, Superoxide and Phototoxicity", Photochemistry and Photobiology, vol. 67, No. 4, pp. 399-403 (1998).
N. P. S. Cheruvu et al.: "Effect of Eye Pigmentation on Transscleral Drug Delivery", Invest Ophthalmol Vis Sci., vol. 49, No. 1, pp. 333-341 (2008).
R. F. Jameson et al.: "Complex Formation Followed by Internal Electron Transfer: The Reaction Between Cysteine and Iron (III)", Chemical Monthly, vol. 122, pp. 887-906 (1991).

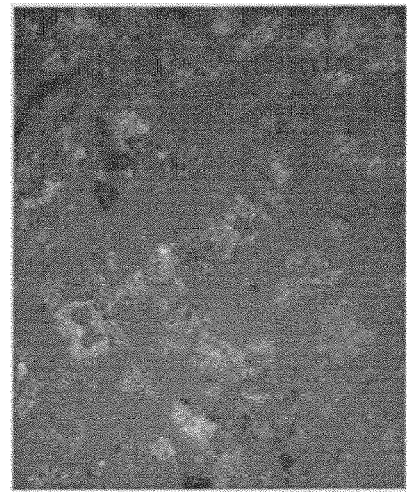
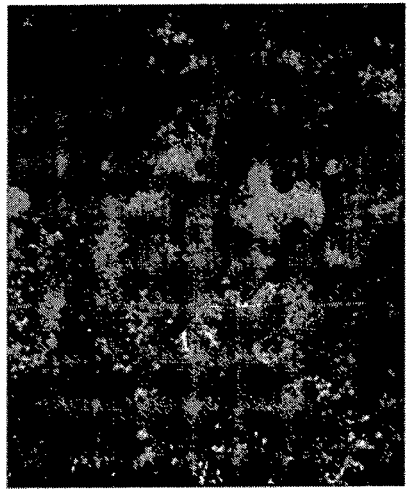
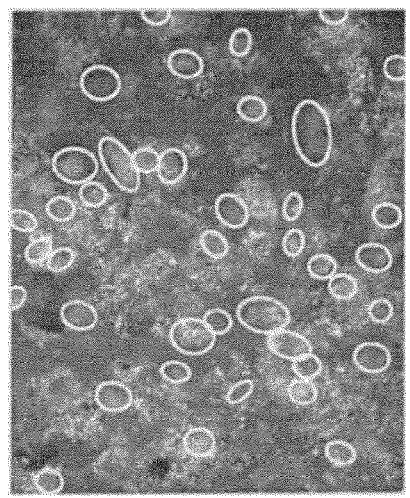
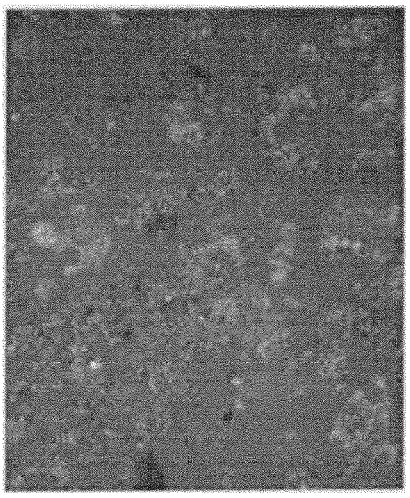
human RPE cell culture after one week
A: SAD 50microg/ml
B: SAD + Cardioxane 10 microM
C: SAD + Cardioxane 50 microM
D: SAD + Cardioxane 100 microM
Fig. 2 A to D

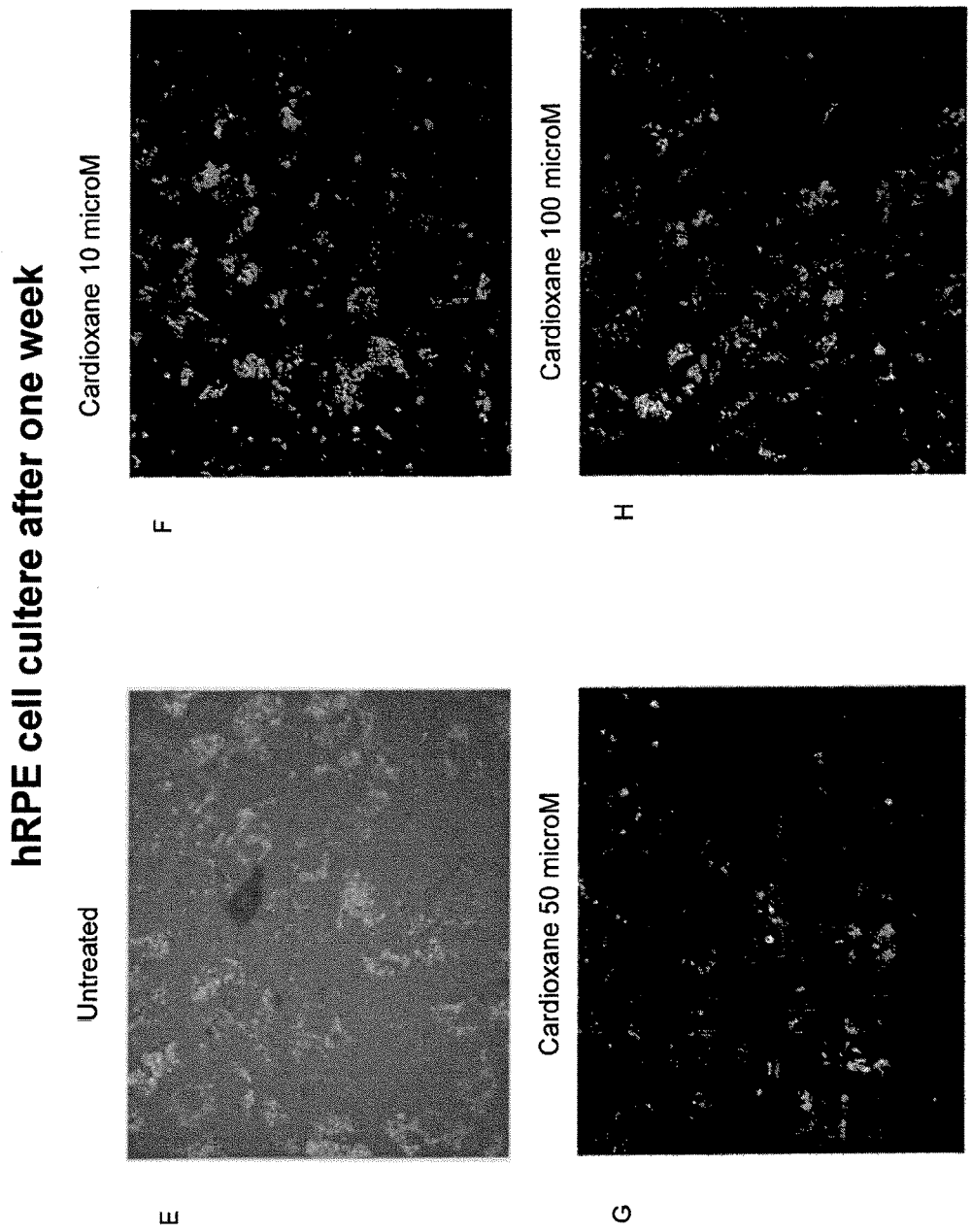
Fig. 2 (continued) E to H

METHODS FOR THE DETERMINATION OF COMPOUNDS OR COMPOSITIONS FOR THE TREATMENT OF LIPOFUSCIN RELATED DISEASES AND COMPOUNDS OR COMPOSITIONS

FIELD OF THE DISCLOSURE

The present invention concerns the field of lipofuscin associated diseases of the central nervous system (CNS) and the eye of mammals. It inter alia provides methods for selecting novel compounds for the treatment of lipofuscin associated diseases as well as compounds and compositions for the treatment determined by the method.

BACKGROUND OF THE INVENTION

Lipofuscin is a general term to describe lysosomal deposits of insoluble materials that accumulate in the tissues of organisms in the process of aging or due to genetic deficiencies in common hydrophobic clearance mechanisms (e.g. mutations of ABC transporters). In its broadest sense, the accumulation of critical amounts of lipofuscin is pathologic in any tissue, but especially so in the tissues of the CNS where the loss of cell function through lipofuscin is particularly apparent.

Lipofuscin is a lipid rich substance which is found to be accumulated in post mitotic cells of e.g. the brain, the heart, or the retinal pigment epithelium in the eye over a life time. The composition is complex and still under investigation. In the eye, one important and well characterized component of lipofuscin is the flurophore N-retinylidene-N-retinylethanolamine (A2E), a byproduct of the visual cycle. It can be detected histologically by its autofluorescence properties. The origin of lipofuscin in the RPE is still under debate (C J Kennedy, P E Rakoczy and I J Constable, 'Lipofuscin of the Retinal Pigment Epithelium: A Review', *Eye (London, England)*, 9 (Pt 6) (1995), 763-771.).

Lipofuscin is particularly formed in tissues with high oxidative stress (A Terman and U T Brunk, 'Lipofuscin: Mechanisms of Formation and Increase with Age', *APMIS: acta pathologica, microbiologica, et immunologica Scandinavica*, 106 (1998), 265-276.). It accumulates progressively over time in lysosomes of post mitotic cells, such as neurons and cardiac myocytes and the retinal pigment epithelium (RPE). The exact mechanisms behind this accumulation are still unclear and may vary in different diseases. Numerous studies indicate that the formation of lipofuscin is due to the oxidative alteration of macromolecules by oxygen-derived free radicals generated in reactions catalyzed by redox-active iron of low molecular weight. Two principal explanations for the increase of lipofuscin with age have been suggested. The first one is based on the notion that lipofuscin is not totally eliminated (either by degradation or exocytosis) even at a young age, and, thus, accumulates in postmitotic cells as a function of time. Since oxidative reactions are obligatory for life, they would act as age-independent enhancers of lipofuscin accumulation, as well as of many other manifestations of senescence. The second explanation is that the increase of lipofuscin is an effect of aging, caused by an age-related enhancement of autophagocytosis, a decline in intralysosomal degradation, and/or a decrease in exocytosis.

One general function of the metabolism is to maintain compounds in solution to allow them to be cleared by solution mechanisms (e.g. urine) or efflux mechanisms as carried out by ABC transporters. For this function, the cell contains enzymes for oxidising and conjugating even lipophilic compounds. However, particularly lipophilic components such as pigments are susceptible to redox reactions which may lead to cross-linking and consequent precipitation. Once precipitated, hydrophobic interactions stabilise the precipitate and thereby present few or no sites where the material can interact with the generally deep reaction pockets of hydrolytic enzymes. Hydrophobic deposits are, in turn, likely to further interact with and precipitate other hydrophobic species. Thus, lipofuscin accumulation represents a stabilised form of hydrophobic detritus that appears inaccessible to normal metabolic clearance by enzymes.

Lipofuscinoses and lipofuscinopathies are, therefore, diseases characterised by high levels of lipofuscin deposits as a result of aging, or metabolic defects. Lipofuscin associated degenerative diseases of the eye have in common that lipofuscin is accumulated in the cells of the RPE. Such diseases include age-related macular degeneration, Stargardt's disease, Best's disease and subpopulations of Retinitis pigmentosa.

In age-related macular degeneration (AMD), early stages with full visual capacity of patients are distinguished from advanced stages with beginning to severe visual impairment. For advanced stages of AMD, atrophic AMD with geographic atrophy and exudative AMD (or synonymous wet, neovascular AMD) with choroidal neovascularization are differentiated. Typically but not in all cases, atrophic AMD occurs in the eye before development of the exudative form. All early stages of AMD and advanced atrophic AMD are usually summarized as dry AMD (see FIG. 1). All stages of AMD are characterized by drusen formation and lipofuscin accumulation in RPE cells. Advanced dry AMD is in addition characterized by the complete and irreversible degeneration of the neuroretina tissue forming sharply demarcated areas of RPE atrophy, the so called geographic atrophy. Geographic atrophy extending to the macula, the area of the retina responsible for visual acuity (FIG. 1), will seriously affect the ability to read, recognize faces or pursue everyday activities such as walking, driving, or shopping. As such, the impact of AMD on quality of life and patient independence can be devastating. In wet AMD, in addition to the characteristics of early AMD and usually also advanced dry AMD, neovascularization takes place.

Stargardt's disease (disease code H35.5 according to ICD-10) is a severe inherited juvenile macular degeneration due to autosomal recessive mutation of the ABCA4 gene or autosomal dominant mutation of the ELOVL 4 gene. It begins in late childhood. Along with progression of the disease, lipid rich deposits (lipofuscin) accumulate in the retinal pigment epithelium (RPE) layer beneath the macula. In advanced Stargardt's disease, the build-up of lipofuscin causes atrophy of the RPE and subsequently the macula supplied by this area of the RPE. At the final stage, Stargardt's disease leads to legal blindness.

Best's disease, also termed vitelliform macular dystrophy or vitelliform dystrophy, is a retinal lipofuscinosis leading to progressive vision loss in the macula. The early-onset form, Best disease, is caused by mutations of the gene encoding the chloride transporter bestrophin, VMD2, and usually appears in childhood, The late-onset form begins in middle age, and tends to be more mild and is associated in ca. 25% of cases with mutations of VMD2 or RDS (peripherin).

Retinitis pigmentosa (RP) is a group of inherited disease of the retina. RP patients develop a degeneration of the photoreceptors and retinal pigment epithelium (RPE) cells. RP culminates in the degeneration of the photoreceptors in the fovea reducing central vision. RP is one of the main causes of acquired blindness in developed countries. Abnormal levels of lipofuscin accumulation are observed in more than one-half of RP patients.

Lipofuscin associated diseases are also found in other tissues. For example, neuronal ceroid lipofuscinoses (NCL) is the general name for a family of at least eight genetically separate neurodegenerative disorders that result from excessive accumulation of lipofuscin in the body's tissues. The neuronal ceroid-lipofuscinoses (NCLs) are characterized by progressive intellectual and motor deterioration, seizures, and early death. Visual loss is a feature of most forms.

The primary cause responsible for Alzheimer's disease (AD) remains unknown. Aβ protein has been identified as the main component of amyloid of senile plaques, the hallmark lesion of AD, but it is not certain whether the formation of extracellular Aβ deposits is the main cause of the series of pathological events in the brain in the course of sporadic AD.

Lipofuscin is a relatively overlooked age-related product and the hypothesis was formulated that its release into the extracellular space following the death of neurons may contribute to the formation of senile plaques. The presence of intraneuronal Aβ, similarities between AD and age-related macular degeneration, and the possible explanation of some of the unknown issues in AD suggest that a contribution of lipofuscin to AD pathology should be considered (Giorgio Giaccone and others, 'Lipofuscin Hypothesis of Alzheimer's Disease', *Dementia and Geriatric Cognitive Disorders Extra*, 1 (2011), 292-296 <doi:10.1159/000329544>.). At the same time, negative effects of lipofuscin on e.g. proteasomal system have been established (Annika Höhn and Tilman Grune, 'Lipofuscin: Formation, Effects and Role of Macroautophagy', *Redox biology*, 1 (2013), 140-144 <doi:10.1016/j.redox.2013.01.006>.).

It has been found that tetrahydropyridoethers (THPEs), in particular (7R,8R,9R)-2,3-Dimethyl-8-hydroxy-7-(2-methoxyethoxy)-9-phenyl-7,8,9,10-tetrahydro-imidazo[1,2-h] [1,7]naphthyridine (INN Name: Soraprazan) and its salts and related compounds remove natural lipofuscin from RPE cells and can therefore serve as active ingredient in the treatment of AMD degeneration, in particular of dry AMD and Stargardt's disease (EP 2080513 A1). The effect has been observed in healthy monkeys removing naturally accumulated lipofuscin (Sylvie Julien and Ulrich Schraermeyer, 'Lipofuscin Can Be Eliminated from the Retinal Pigment Epithelium of Monkeys', *Neurobiology of aging*, 33 (2012), 2390-2397 <doi:10.1016/j.neurobiolaging.2011.12.009>.), in human RPE cells from aged donors (S. Julien and others, 'Lipofuscin Can Be Eliminated From Retinal Pigment Epithelium After Drug Treatment', *ARVO Meeting Abstracts*, 51 (2010), 481.), and in mice exhibiting a gene defect thought to serve as a model for Stargardt's Disease. However, the mode of action of the THPE compounds was unknown.

SUMMARY OF THE INVENTION

According to a first aspect the invention provides a method for selecting a compound or a composition suitable for treating lipofuscin associated diseases in a patient comprising the steps of
a) determining a reactivity factor,
b) determining a targeting actor, that allows an uptake into a cell and provides a targeting of lipofuscin,
c) selecting a compound or a composition or combining compounds to obtain a compound or composition that comprises a reactivity factor and an targeting factor.

It was surprisingly found that compounds and compositions that comprise the combination of a reactivity factor, as e.g. a radical providing agent, and a targeting factor, as e.g. lipophilicity of the molecule, are able to degrade lipofuscin in cells. The provided method allows simple identification of active ingredients for the treatment of lipofuscin associated diseases.

The reactivity factor is preferably a radical providing agent. The reactivity factor may therefore oxidize lipofuscin and consequently cause a degradation and dissolution of lipofuscin aggregates. As shown e.g. in example 1 a radical scavenger abolishes the degradation of the lipofuscin caused by the test compound. In order to oxidize the lipofuscin the reactivity factor has to be in proximity to the lipofuscin deposits, and thus has to enter a cell containing lipofuscin and target the lipofuscin in the cell. The targeting factor according to the invention allows an entry of the compound or composition in into a cell and guarantees a targeting of the compound or composition to the lipofuscin in the cell.

Thus, the present invention applies the obtained knowledge about the mechanism of lipofuscin degradation to provide an easy method for the selection of compounds that are suitable for treating lipofuscin associated diseases in a patient.

According to a second aspect of the invention a compound or composition is provided, comprising at least one reactivity factor, preferably a radical providing agent, and at least one targeting factor, preferably including lipophilicity, that allows an uptake into a cell and a provides a targeting of lipofuscin, for use in the treatment of lipofuscin associated diseases wherein the compound is not a compound of formula (I)

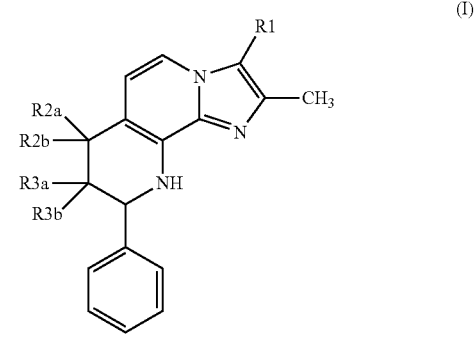

wherein R1 is methyl or hydroxymethyl, one of the substituents R2a and R2b is hydrogen and the other is hydroxy, methoxy, ethoxy, isopropoxy, methoxyethoxy or ethoxypropoxy, one of the substituents R1a and R3b is hydrogen and the other is hydroxy, methoxy, ethoxy, isopropoxy, methoxyethoxy or methoxypropoxy.

According to a third aspect of the invention a compound or composition is provided, comprising at least one permeability factor for use in the treatment of lipofuscin associated diseases

BRIEF DESCRIPTION OF THE FIGURES

FIG. 2A to H show micrographs of RPE of cells after one week of incubation with test compounds and illumination. The images correspond to the following test compounds: A)

50 µg/ml superoxide Anion Donor (SAD), B) 50 µg/ml SAD, 10 µM cardioxane, C) 50 µg/ml SAD, 50 µM cardioxane, D) 50 µg/ml SAD, 100 µM cardioxane, E) no test compound, F), 10 µM cardioxane, G) 50 µM cardioxane, H) 100 µM cardioxane. In the original images, lipofuscin in cells is visible as a yellow-gold-orange fluorescent structure, before the blue background. Areas of degradation of lipofuscin in the hRPE cells appear as bright blue to whitish structures. In the grey scale reproduction in FIG. 2 the yellow-gold-orange structures appear light grey (yellow) or dark grey (gold) before a grey background. The originally bright blue to whitish structures are circled in the grey scale reproduction.

Figure 1:
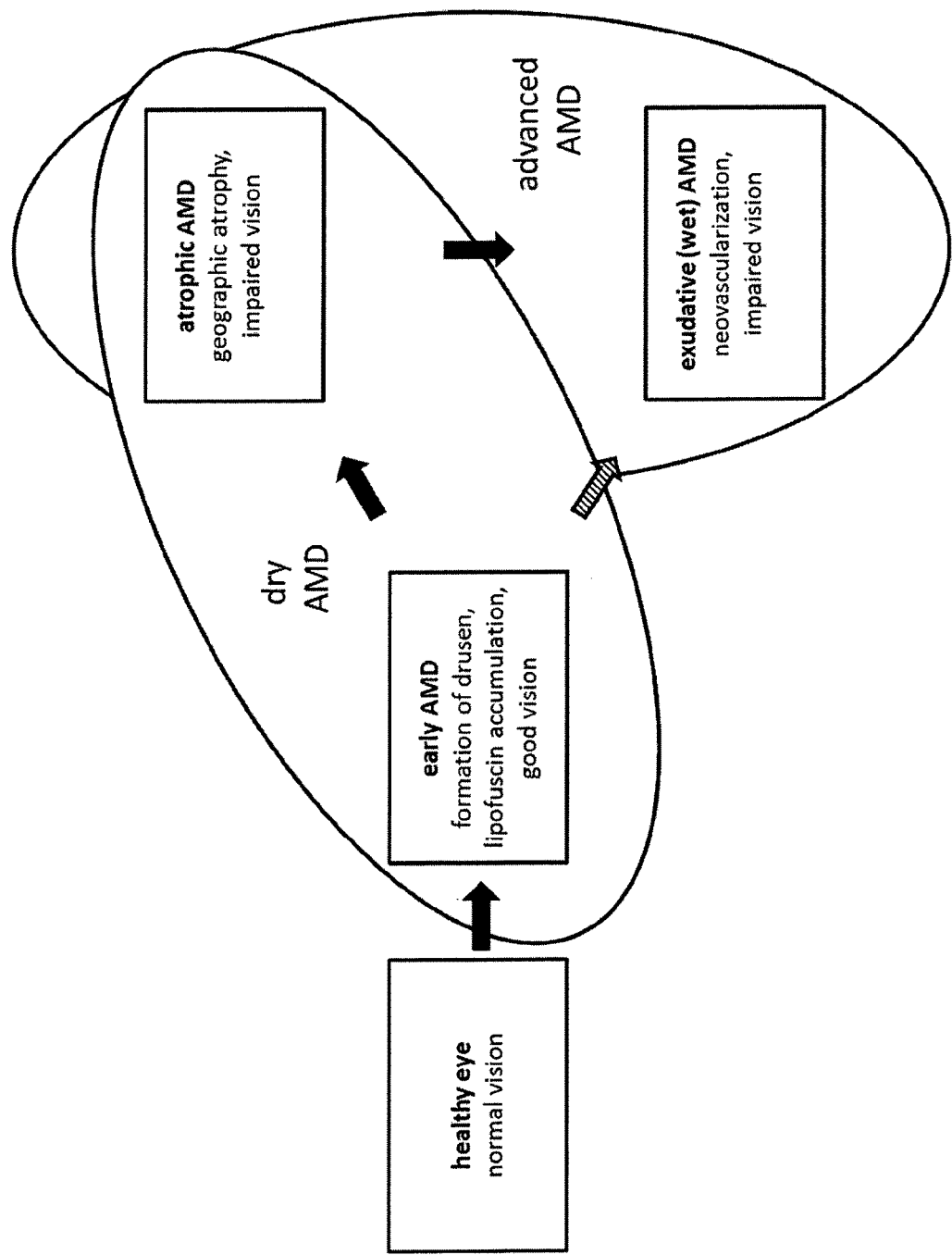
FIG. 1 shows a schematic overview of the different AMD stages
Figure 3:
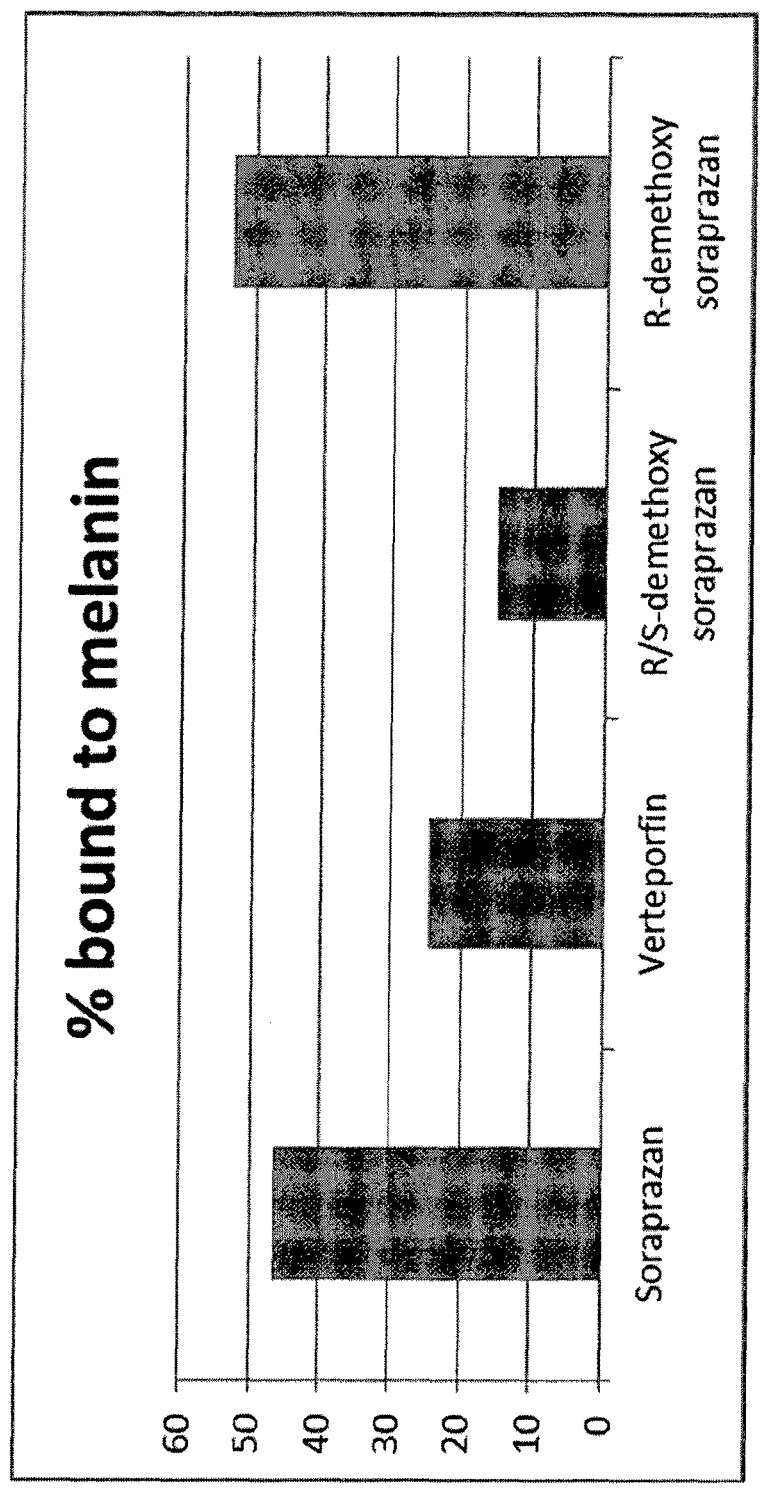
Figure 3:
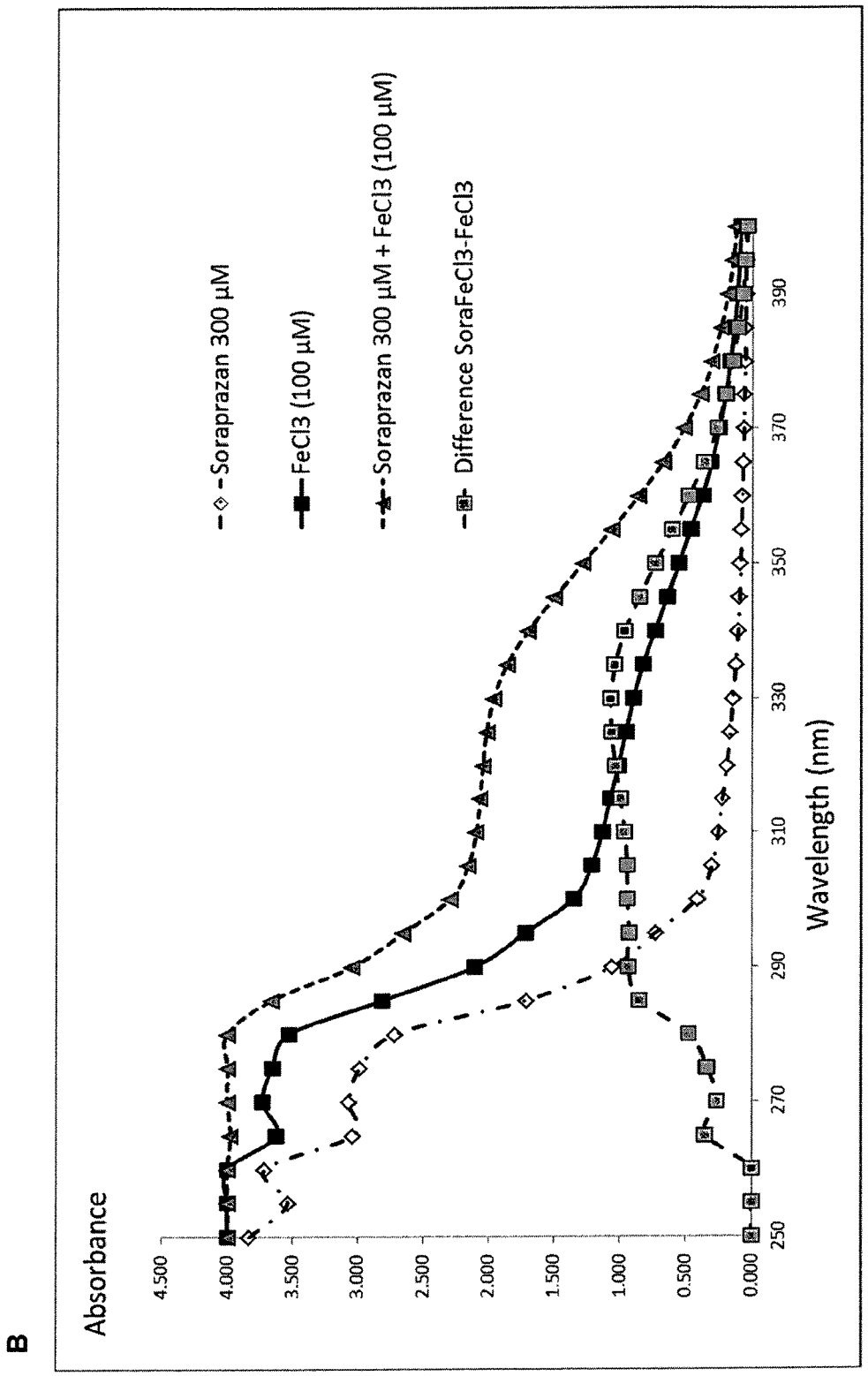

FIG. 3A. shows a column diagram representing the results of the binding study of different compounds with particles of melanin and A2E. The column height indicates the proportion of compound bound to the melanin A2E particle after incubation. FIG. 3B shows the light absorbance spectrum of soraprazan in water alone or in combination with $FeCl_3$ the light absorption spectrum of $FeCl_3$ alone, and the difference spectrum of soraprazan plus $FeCl_3$ and soraprazan.

Figure 4:
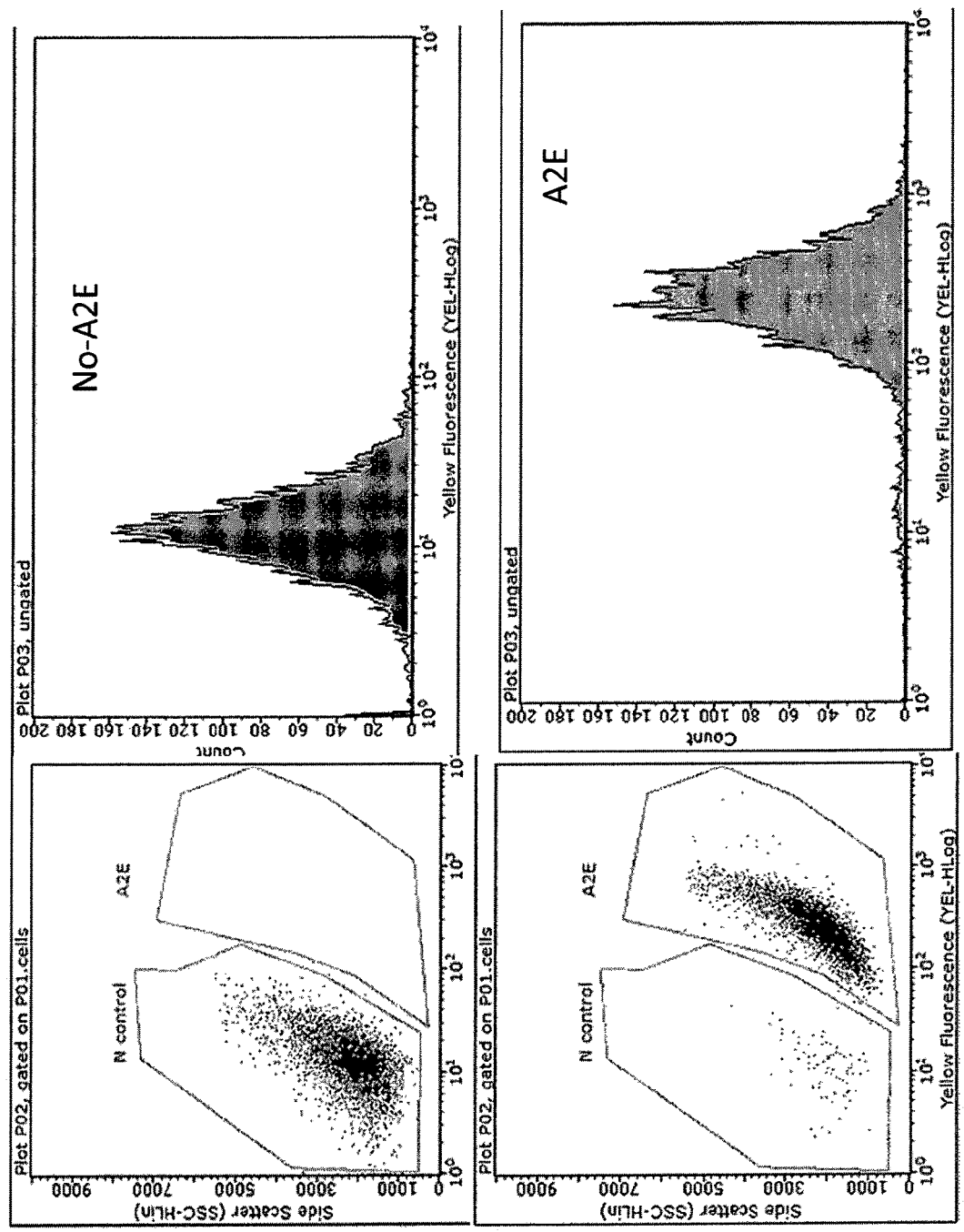

FIG. 4 shows the results of a flow cytometry measurement of ARPE19 cells treated with A2E and untreated ARPE19 cells. These data show that ARPE cells take up A2E which is detectable as a change in fluorescence.

Figure 5:
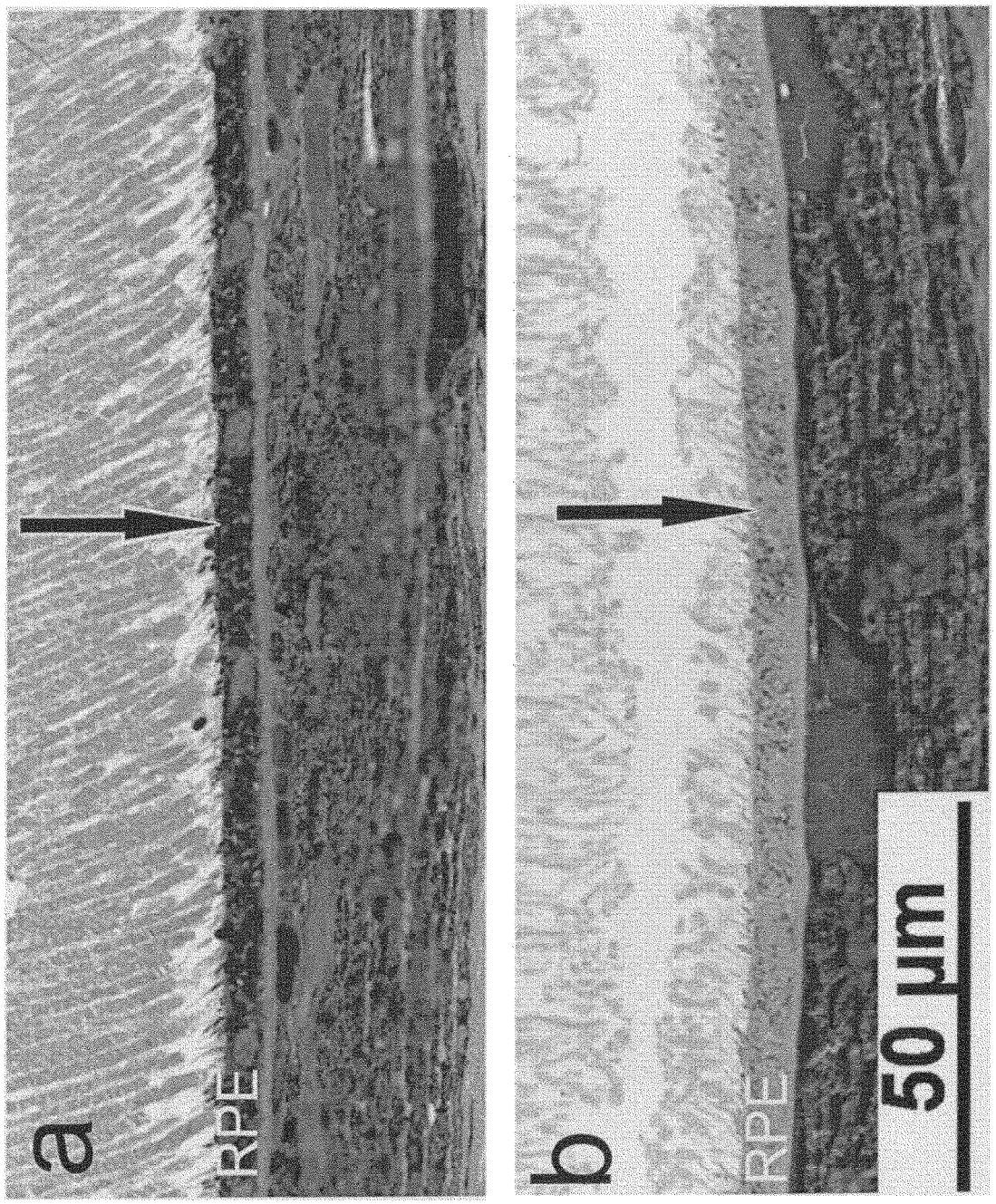

FIG. 5 shows electron micrographs of semi-thin sections of the eyes of mice lacking the the Abca4 transporter either untreated (FIG. 5a) or treated verteporfin (FIG. 5b). The arrow indicates the RPE cell layer. RPE cells of untreated mice are much denser than RPE cells of treated mice.

Figure 6:
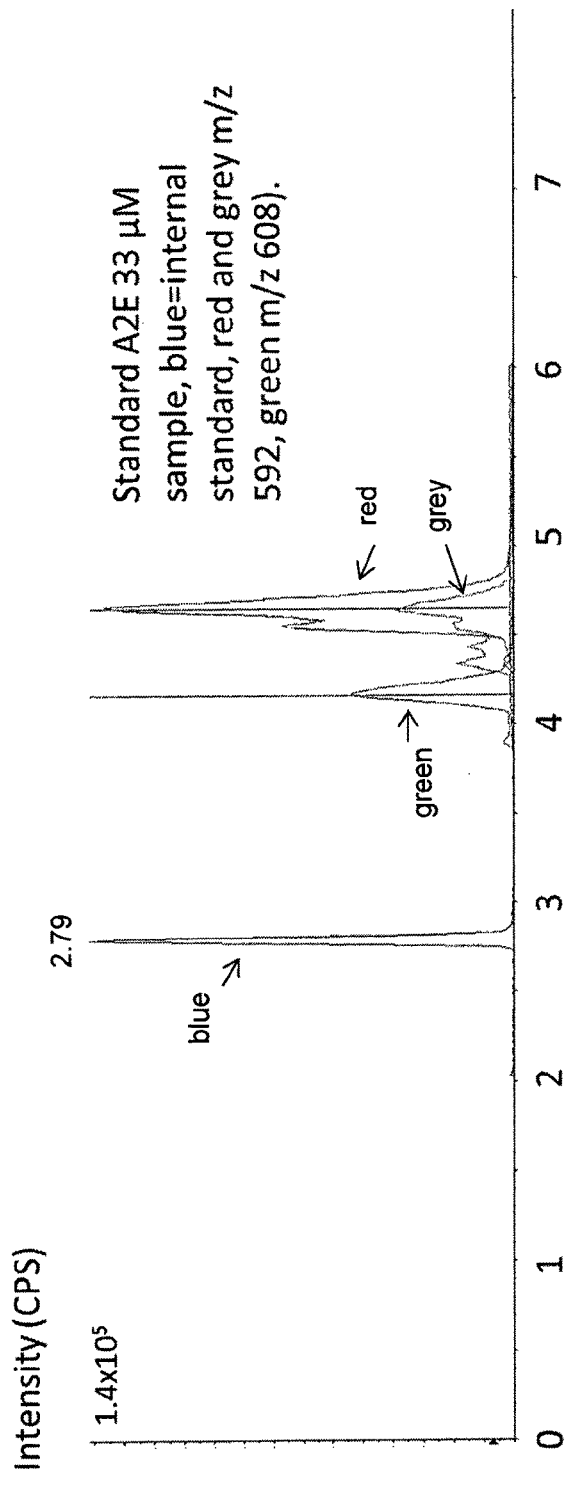

FIG. 6 shows a chromatogram from a separation of standard A2E 33 µM sample, using mass selective detection (blue, internal standard, Red m/z 592, Green m/z 608).

Figure 7:
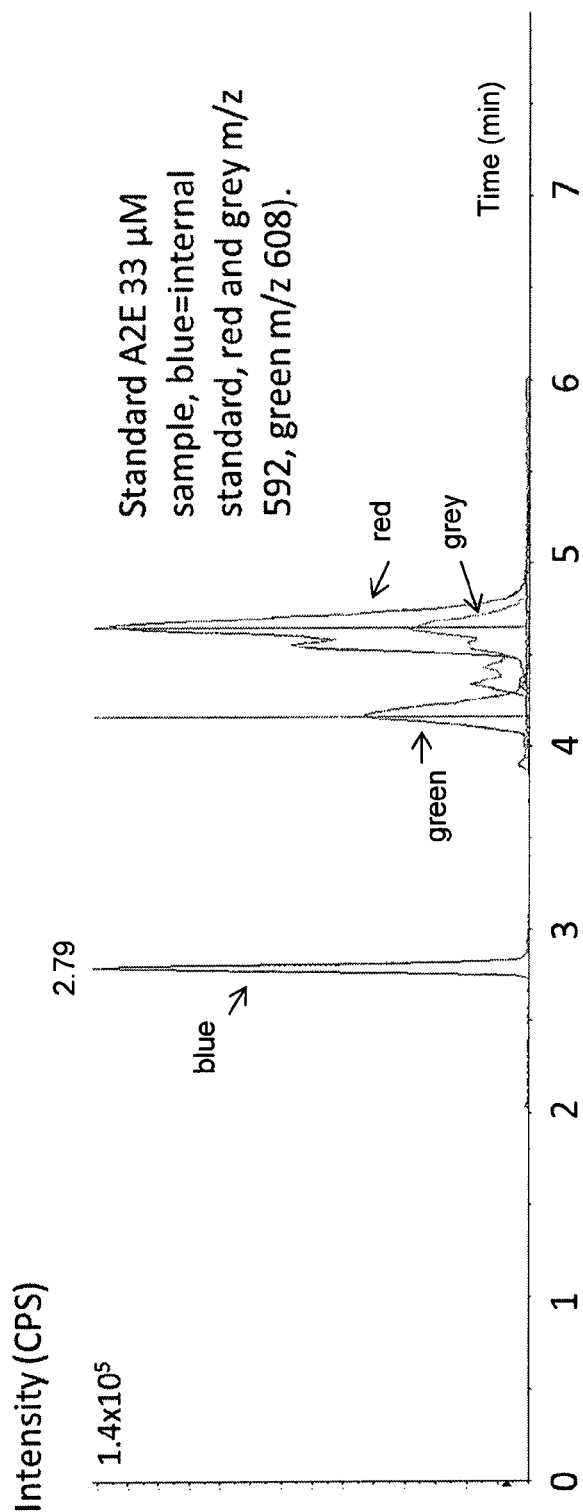

FIG. 7 shows a chromatogram from an eye extract, using mass selective detection (blue, internal standard, Red m/z 592, Green m/z 608).

DETAILED DESCRIPTION OF THE INVENTION

The present invention provides methods for selecting novel compounds for the treatment of lipofuscin associated diseases as well as compounds for the treatment determined by the method. The individual aspects and suitable and preferred embodiments thereof will now be described in detail.

According to a first aspect the invention provides a method for selecting a compound or a composition suitable for treating lipofuscin associated diseases in a patient comprising the steps of
 a) determining a reactivity factor,
 b) determining a targeting factor, that allows an uptake into a cell and a provides a targeting of lipofuscin,
 c) selecting a compound or a composition or combining compounds to obtain a compound or composition that comprises a reactivity factor and an targeting factor.

The method of the first aspect according to the invention is inter alia based on the unexpected finding that a reactivity factor and a targeting factor are sufficient for a compound or composition to effectively degrade lipofuscin deposits.

The reactivity factor according to the invention is an atom or molecule that may initiate, enhance or undergo a reaction with lipofuscin, or components of lipofuscin. The reactivity factor may be an oxidizing agent and/or a radical providing agent.

Examples of reactivity factors enhancing the reaction with lipofuscin are complexed metal ions such as zinc or iron.

According to the most preferred embodiment of the invention, the reactivity factor is a radical providing agent. According to another embodiment the method the reactivity factor is an oxidizing agent. According to another embodiment of the method the reactivity factor is an agent that is photoactive.

The requirement of a reactivity factor is based on the finding that particular members of the family of tetrahydropyridoethers (THPE) are able to degrade lipofuscin and this degradation of lipofuscin deposits relies on the action of radicals. Although it had been shown earlier that in particular soraprazan can actively degrade lipofuscin in the eye and in isolated RPE cells it was assumed that the small molecule might induce a detoxification system, i.e. as a ligand to the nuclear receptor PXR, which controls the expression of many detoxification enzymes.

However, as shown in the examples the lipofuscin component A2E is degraded by soraprazan also in cell free systems suggesting that an induction of a cellular mechanism by the compound and in particular the action of enzymes is not required. Moreover, it was surprisingly found that members of the THPE family are generators of a superoxide anion as demonstrated by studies using electron paramagnetic resonance and spin trapping of the radical products. According to the invention a substance capable of generating radical oxygen species is referred to as superoxide anion donator (SAD) or reactive oxygen donator (ROD).

Furthermore, as shown in the examples a radical scavenger abolishes the degradation of the lipofuscin induced by an SAD. Thus, a radical, i.e. the superoxide anion is necessary for the degradation of lipofuscin seen in the incubation with the SAD. This finding is particularly surprising, because it was hitherto thought that reactive oxygen species mediate the precipitation and accumulation of lipofuscin. Without being bound to theory the following hypothesis for the mechanism of degradation is proposed. The transfer of the radical, i.e. the oxygen to the lipofuscin results in the addition of hydroxyl groups, and the destabilization of double bonds in precipitated pigments, which in turn leads to the dissolution of the deposits. Once the solution of the deposits is started, equilibrium favours their export to the blood or medium. In an organism the solubilized lipofuscin is disposed via the normal excretory routes.

In order to cause a reaction with the lipofuscin in the cell the reactivity factor has to reach the lipofuscin or get in proximity of the lipofuscin. Accordingly, it has to be taken up by a cell and to be targeted to the lipofuscin deposits. A targeting factor or accumulation factor according to the invention allows an uptake into a cell and allows targeting of lipofuscin. In order to target lipofuscin the targeting factor preferably has an affinity for lipofuscin.

Soraprazan is for example taken up by a cell and targeted to the lipofuscin deposits due its lipophilic nature.

Hence, it is determined that compounds or compositions that comprise a reactivity factor, preferably a radical providing agent and additionally comprise a transfer factor that allows the cellular uptake and a targeting of lipofuscin are suitable for the degradation of lipofuscin and accordingly for the treatment of lipofuscin associated diseases. Thus, the unexpected mechanism of lipofuscin degradation described herein and the concluded necessary properties of the compounds or composition allow the finding of further compounds suitable for treating lipofuscin associated diseases. Therefore, the present invention makes an important contribution to the prior art.

Alternatively, the reactivity factor may interact with a metal ion in the lipofuscin structure. Metals are components of lipofuscin involved in the coordination and stabilization of the secondary structure of lipofuscin. Accordingly, an interaction of the reactivity factor with metal ions in the lipofuscin structure, such as chelation or coordination of the metal ions may degrade destabilize the lipofuscin agglomerates and increase the solubility of the lipofuscin components. Thus, according to one embodiment the reactivity factor is a metal interacting agent, in particular a chelator or metal ion coordinator.

According to one embodiment the radical providing agent is a radical. The radical is preferably an oxygen radical. According to an alternative embodiment the radical providing agent is a compound with an ability to generate and/or locally coordinate a radical. Methods to determine the ability of a compound to generate and/or locally coordinate a reactive chemical species are known in the art. For example, when observed using electron paramagnetic resonance, the compound mediates transfer of energy to a spin trap molecule used for the purpose of observing such effects. The radical may be selected from hydroxyl radical (.OH), superoxide anion ($O_2^-$), oxide anion ($O_2^-$), nitric oxide ($NO^-$), hydrogen peroxide ($H_2O_2$), and singlet oxygen ($O_2^*$). According to another embodiment the radical providing agent generates or locally coordinates a radical selected from hydroxyl radical (.OH), superoxide anion ($O_2^-$), oxide anion ($O_2^-$), nitric oxide ($NO^-$), hydrogen peroxide ($H_2O_2$), and singlet oxygen ($O_2^*$).

A radical providing agent according to the invention may be one that generates a radical upon energization of the compound. This energization may be caused by illumination by light. According to one embodiment of the method the ability of the radical providing agent to generate and/or locally coordinate a radical is determined in the presence of visible light. For energization a light source providing to whole spectrum of visible light may be used. Alternatively light sources providing light of specific wavelengths may be employed. According to one embodiment of the method the light has a wavelength in the range from 380 nm to 800 nm. Preferably the light has a wavelength in the range from 650 nm. Most preferably, the light for illumination has a wavelength of less in the range from 380 to 500 nm.

According to one embodiment of the first aspect of the invention the ability of the radical providing agent to generate and/or locally coordinate a radical is determined in the absence of visible light. A radical providing agent determined by the method according to the invention may also be energized by chemical processes such as cellular respiration and reductases.

In a composition selected by the method according to the invention the reactivity factor and the targeting factor may be contained in the same or a different compound.

A targeting factor according to the invention most preferably targets lipofuscin due lipophilic interactions. Lipofuscin is lipophilic and thus a lipophilic compound will have an affinity to lipofuscin. On the other hand a targeting factor according to the invention may bind to lipofuscin or components of lipofuscin due to specific interactions that rely on specific moieties of lipofuscin. For example, an antibody or a small molecule with affinity to lipofuscin, may be a targeting factor according to the invention that specifically recognizes components of the lipofuscin deposits. According to one embodiment the targeting factor may have an affinity for, or interact with metal ions in the lipofuscin agglomerate.

According to one embodiment of the first aspect of the invention the targeting factor provides an affinity constant to the compound equal to or below 100 μM. Such an affinity of the compound to lipofuscin provides a strong indication that the compound will stabilize the reactive chemical species sufficiently long in proximity to lipofuscin to allow a transfer of the reactive chemical species. Preferably, the affinity constant is equal to or below 10 μM. More preferably the affinity constant is equal to or below 1 μM. Most preferably the affinity constant is equal to or below 0.1 μM. The lower the affinity constant of the compound, the stronger is the binding of the compound to lipofuscin. A stronger binding leads to a longer contact of the compound or composition to lipofuscin and increases the chance to transfer the reactive chemical species to the lipofuscin.

According to one embodiment of the first aspect of the invention the ability of the targeting factor to target lipofuscin is determined by incubating a defined amount of a potential targeting factor with a suspension of lipofuscin in water, removing the water and measuring the concentration of substance in both the water and the lipofuscin fraction. A targeting factor according to the invention binds at least partially to the lipofuscin fraction. Preferably, at least 5%, at least 10%, at least 20%, at least 30%, at least 40%, at least 50%, at least 60%, at least 70%, at least 80%, at least 90%, or at least 95% of the targeting factor binds to the lipofuscin fraction.

As defined above the targeting factor preferably does not only provide a targeting of lipofuscin in the cell. In addition, the targeting factor may also allow an uptake into the cell. The uptake into the cell may for example occur by endocytosis, active or passive membrane transport. According the one embodiment of the invention the uptake of the targeting factor into the cell is determined by culturing one or more cells in the presence of a potential targeting factor and measuring the concentration increase of the targeting factor in the cell. Such an experiment is also described in the examples. The increase in concentration defines the cellular uptake. The uptake of the targeting factor is preferably such that the concentration of the targeting factor in the cell is at least 10%, at least 20%, at least 30%, at least 40%, at least 50%, at least 60%, at least 70%, at least 80%, at least 90% of the concentration of the targeting factor in the environment. Most preferred, the concentration of the targeting factor in the cell is at least 20% of the concentration of the targeting factor in the environment. The uptake rate is the increase in concentration over time. According to one embodiment a cell of the eye or the CNS of a mammal are used in the test for determining the cellular uptake of a potential targeting factor. Preferably, the cells are human cells.

According to one embodiment the cell is a cell of the retinal pigment epithelium (RPE). Most preferably, the cell is a human RPE cell line. The initial uptake rate of the targeting factor in a human RPE cell line is defined as the change in concentration in a cell over time preferably at least 50 nM/h, more preferably at least 150 nM/h, most preferably at least 250 nm/h.

In order to use a compound or composition comprising a reactivity factor and a targeting factor in therapy the compounds or composition has to be tolerated by the cell, e.g. has to be non-toxic for the cells. A low tolerance of the compounds or compositions might lead to strong side effects. Thus, according to one embodiment of the invention the tolerance of the cell of the eye or the CNS to the targeting and the reactivity factor is determined and a compound or a composition is selected or compounds are combined to obtain a compound or composition that comprises a reactivity factor and an targeting factor that are tolerated by the cell. Such an additional step helps avoiding the selection of compounds or composition that are for example toxic to the cells.

According to one embodiment of the first aspect of the invention the method comprises the step of determining the elimination of lipofuscin or a lipofuscin marker in vitro by said compound, and selecting a compound additionally based on a predefined elimination threshold. The predefined threshold is dependent on the method for determining the elimination rate. A reasonable value for the threshold can be obtained by performing a specific method for eliminating lipofuscin in vitro or the lipofuscin marker with an SAD known to eliminate lipofuscin also in vivo. In the examples several methods are described to test the elimination of the lipofuscin in cell culture. According to one embodiment the step of determining the elimination of lipofuscin comprises the incubation of the compound with cells selected from retinal epithelial cells that have been incubated with the A2E, retinal epithelial cells that have been incubated with animal lipofuscin, retinal epithelial cells that have been incubated with human lipofuscin, retinal epithelial cells that have been harvested from an animal retinal epithelial cells that have been harvested from human donors.

One of the components of the cells derived from the eye is N-retinylidene-N-retinylethanolamine (A2E). As shown in the examples soraprazan which is known to eliminate lipofuscin in cells also degrades A2E in solution under illumination by visible light. Thus, the elimination of lipofuscin can be mimicked by A2E in solution. According to the most preferred embodiment of the invention the lipofuscin marker is A2E. The determination of the degradation of A2E has the advantage to be faster than methods including the growth of cells. Moreover, the use of A2E allows a simple determination of the degradation rate. For example, to A2E in solution a potential compound may be added. This mixture may then be illuminated for a predetermined time. According to the most preferred embodiment of the method the step of determining the elimination of A2E comprises the incubation of the compound with A2E in the presence of light. Suitable lamps for illumination are known in the art and do not require further explanation. The illumination time is preferably 1 min or 5 min. According to one embodiment of a wavelength of 689 nm for 1 min. According to another embodiment the mixture of A2E and the potential compound is illuminated with white light for 5 min. Alternatively, the mixture of A2E and the potential compound may also be incubated with substance that chemically energizes the potential compound. The chemically energizing substance may be an oxidizing agent such a hydrogen peroxide ($H_2O_2$). According to one embodiment of the method the step of determining the elimination of A2E comprises the incubation of the compound with A2E in the presence of hydrogen peroxide $H_2O_2$. After illumination or incubation the sample may be analyzed by liquid chromatography and mass spectroscopy. Suitable devices for carrying out a combined liquid chromatography and mass spectroscopy are known in the art.

A potential candidate compound tested by the method of selection according to the invention may be any compound. Preferably the potential compound is selected from compounds that are able to absorb light and which are cell permeable. More preferably the compound is selected from the classes quinones, flavones, flavins, amino acids, bile acids, aromatic amino acids, pyroles, porphyrins, dioxetanes, photosensitizers, quinolones, quinidines, NSAIDS, psoralens, retinoic acids, and melanizing agents, tetracycline antibiotics, redox active proteins, redox active small molecules, dyes, and metal interacting agents.

With the method according to the first aspect of the invention compounds and compositions that are suitable for the treatment of lipofuscin associated diseases can be selected. Thus, according to a second aspect of the invention a compound or composition is provided comprising at least one reactivity factor and at least one targeting factor that allows an uptake into a cell and provides a targeting of lipofuscin, for use in the treatment of lipofuscin associated diseases wherein the compound is not a compound of formula (I)

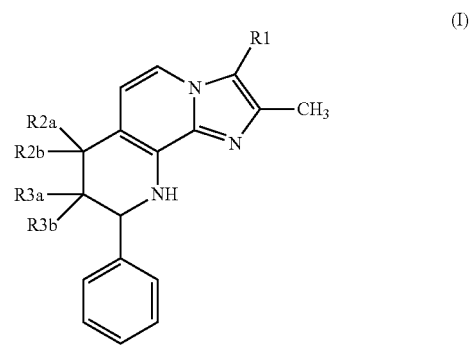

wherein R1 is methyl or hydroxymethyl, one of the substituents R2a and R2b is hydrogen and the other is hydroxy, methoxy, ethoxy, isopropoxy, methoxyethoxy or ethoxypropoxy, one of the substituents R3a and R3b is hydrogen and the other is hydroxy, methoxy, ethoxy, isopropoxy, methoxyethoxy or methoxypropoxy.

The compound or composition according to the second aspect of the invention fulfills in particular the properties defined in the method of selection.

The reactivity factor of the compound or composition may be an oxidizing agent or a radical providing agent. According to a preferred embodiment of the second aspect of the invention the radical providing agent is a radical. The radical preferably is an oxygen radical. According to an alternative preferred embodiment the radical providing agent is a molecule with ability to generate and/or locally coordinate a radical. The radical may be selected from hydroxyl radical (.OH), superoxide anion ($O_2^-$), oxide anion ($O_2$—), nitric oxide ($NO^-$), hydrogen peroxide ($H_2O_2$), and singlet oxygen ($O_2^*$). According to another embodiment of the second aspect the radical providing agent generates or locally coordinates a radical selected from hydroxyl radical (.OH), superoxide anion ($O_2^-$), oxide anion ($O_2$—), nitric oxide ($NO^-$), hydrogen peroxide ($H_2O_2$), and singlet oxygen ($O_2^*$).

The radical providing agent of the compound or composition according to the second aspect may be one that generates the radical upon energization of the compound. This energization may be caused by illumination with light. The reactivity factor may initiate or only enhance a reaction or participate in a reaction of an atom or molecule with lipofuscin. Examples of reactivity factors enhancing the reaction with lipofuscin are complexed metal ions such as zinc or iron. According to another embodiment of the second aspect the radical providing agent generates and optionally locally coordinates the radical in the presence of visible light. For energization a light source providing the whole spectrum of visible light may be used. According to one embodiment of the compound for use the light has a wavelength of less than 800 nm. Preferably the light has a wavelength of less than 650 nm. Most preferably, the light for illumination has a wavelength of less than 500 nm.

According to an alternative embodiment according to the second aspect of the invention the compound or composition comprises a reactivity factor, preferably a radical providing agent that generates and optionally locally coordinates the reactive chemical species in the absence of visible light. The reactivity factor, in particular the radical providing agent according to the invention may also be energized by chemical processes such as respiration or cellular reductases.

According to one embodiment of the second aspect the targeting factor provides an affinity constant to the compound or composition that is equal to or below 100 µM. Preferably, the affinity constant is equal to or below 10 µM. More preferably the affinity constant is equal to or below 1 µM. Most preferably the affinity constant is equal to or below 0.1 µM.

According to one embodiment of the second aspect of the invention the ability of the targeting factor to target lipofuscin is defined by its ability to bind lipofuscin after incubation with a suspension of lipofuscin in water, and separation of the water and the lipofuscin fraction. A targeting factor according to the invention binds at least partially to the lipofuscin fraction. Preferably, at least 5%, at least 10%, at least 20%, at least 30%, at least 40%, at least 50%, at least 60%, at least 70%, at least 80%, at least 90%, or at least 95% of the targeting factor binds to the lipofuscin fraction.

According the one embodiment of the second aspect the uptake of the targeting factor into the cell is determined by culturing one or more cells in the presence of a potential targeting factor and measuring the concentration increase of the targeting factor in the cell. The uptake of the targeting factor is preferably such that the concentration of the targeting factor in the cell is at least 20% of the concentration of the targeting factor in the environment. The uptake rate is the increase in concentration over time. According to one embodiment cell of the eye or the CNS of a mammal are used in test for determining the cellular uptake of a potential targeting factor. Preferably, the cells are human cells, According to one embodiment the cell is a cell of the retinal pigment epithelium (RPE). Preferably, the cell is a human RPE cell line. The initial uptake rate (change in concentration following introduction of a substance to the medium) of the targeting factor in a human RPE cell line is preferably at least 50 nM/h, more preferably at least 150 nM/h, most preferably at least 250 nM/h.

According to one embodiment of the compound or composition for use, the compound is selected from the light absorbing agents: quinones, flavones, flavins, amino acids, bile acids, dyes, aromatic amino acids, pyroles, porphyrins, dioxetanes, photosensitizers, quinolones, quinidines, NSAIDS, psoralens, retinoic acids, and melanizing agents, tetracycline antibiotics, redox active proteins, redox active small molecules, and metal interacting agents.

Preferred amino acids are cysteine and tryptophan. Preferred metabolites are riboflavin and glutathion. A preferred quinolone is fleroxacin. Preferred dyes are indocyanine green, crystal violet, quinine, fluorescein rose bengal. phenothiazine Preferred tetracycline antibiotics are chloramphenicol, doxycycline, and demeclocycline. Preferred metal interacting agents are taurodeoxycholate EDTA and 1,10-phenanthroline.

According one embodiment of the compound or composition for use, the composition comprises two or more reactivity factors and at least one targeting factor that allows an uptake into a cell and provides a targeting of lipofuscin, for use in the treatment of lipofuscin associated diseases. Preferably, one reactivity factor is a complexed metal ion, such as zinc or iron. As shown in the examples complexed metal ions, in particular Fe (III) may enhance the absorption of radical providing agents such as SADs. According to a more preferred embodiment the first reactivity factor is a complexed metal ion and the second reactivity factor is an SAD. More preferably, the second reactivity factor is a THPE, most preferably the second reactivity factor is soraprazan. According to one embodiment the composition for use comprises soraprazan and Fe (III), preferably in a molar ratio of 3:1.

According to one embodiment of the compound or composition for use, the composition comprises a complexed metal ion selected from iron or zinc. The iron can be Fe (II) or Fe (III). Preferably the iron is Fe (III). According to one embodiment of the compound or composition for use, the composition comprises a compound selected form quinones, flavones, flavins, dyes, aromatic amino acids, pyroles, porphyrins, dioxetanes, photosensitizers, quinolones, quinidines, NSAIDS, psoralens, retinoic acids, and melanizing agents, complexed with a metal ion, in particular Fe (III). As shown in FIG. 3B the Fe (III) may enhance the light absorbance of an SAD, in particular soraprazan.

According to another embodiment of the compound or composition for use the compound is selected from hypericin, rose bengal diacetate, merocyanine 540, malachite green, 1,10-phenanthroline iodoacetamide, aminolevulinic acid, methyl aminolevulinate, porfimer sodium, talaporfin, temoporfin, methylene blue, riboflavin and tryptophan. Riboflavin and tryptophan are natural metabolites of the cells and thus are highly tolerated by the cells. In a preferred embodiment the compound is selected from riboflavin and tryptophan.

According to one embodiment of the compound or composition for use the treatment of lipofuscin related diseases includes a decrease of cellular lipofuscin in the cells of a patient. Decrease of cellular may be a decrease in size of lipofuscin aggregates and/or the reduction of the amounts of lipofuscin aggregates. Preferably, the treatment of a lipofuscin related disease includes elimination of lipofuscin aggregates.

According to a one embodiment of the second aspect of the invention the lipofuscin associated disease is a disease of the eye or of the CNS of patient. Preferably lipofuscin associated disease is a disease of the eye. More preferably, the lipofuscin associated disease is a disease of the eye selected from age-related macular degeneration (AMD), Stargardt's disease, Best's disease and Retinitis pigmentosa.

In preferred embodiment of the compound or composition for use the targeting factor is lipophilic and the reactivity factor is a compound selected from hypericin, rose bengal diacetate, merocyanine 540, malachite green, 1,10-phenanthroline iodoacetamide, aminolevulinic acid, methyl aminolevulinate bergapten, methoxsalen, porfimer sodium, psoralene, talaporfin, temoporfin, methylene blue, riboflavin and tryptophan.

In a more preferred embodiment the of the compound or composition for use the targeting factor is lipophilic and the reactivity factor is a compound selected from hypericin, rose bengal diacetate, merocyanine 540, malachite green, 1,10-phenanthroline iodoacetamide, aminolevulinic acid, methyl aminolevulinate bergapten, methoxsalen, porfimer sodium, psoralene, talaporfin, temoporfin, methylene blue, riboflavin and tryptophan and the lipofuscin associated disease is age-related macular degeneration (AMD).

According to one embodiment the compound or composition for use is not verteporfin. According to a further embodiment if the lipofuscin related disease is AMD and the compound for use is verteporfin then the treatment does not include an illumination time of 83 s and an illumination wavelength of 689±3 nm.

The compound or composition may be administered to the patient for treating a lipofuscin associated disease according to any known route of administration. Exemplary routes of administration are oral, parenteral, mucosal, enteral or percutaneous. The compound or composition may be administered orally in form of, e.g. a pill, a capsule or in liquid form. Parenteral forms of administration include injecting the compound or composition into a vein (intravenous). According to one embodiment of the second aspect the treatment comprises administering an intravenous injection of the compound or composition to a patient with a retinal lipofuscinopathy. Alternatively the compound or composition may be administered by direct injection into the involved tissue e.g. the vitreous (intravitreal) or the conjunctive (conjunctival). According to one embodiment of the compound or composition for use the treatment comprises administering an intravitreal injection of the compound or composition to a patient with a retinal lipofuscinopathy. This route of administration is associated with a lower overall dose, a higher concentration at the site of disease and lower systemic exposure. Other parenteral forms of administration are e.g. intramuscular, intrarterial, intrperitoneal, intracardiac and subcutaneous.

The treatment may further comprise an illumination of the eye with visible light. For illumination a light source providing the whole spectrum of visible light may be used. Alternatively light sources providing light of specific wavelengths may be employed. According to one embodiment of the method the light has a wavelength of in the range from 380 nm to 800 nm. Preferably the light has a wavelength in the range from 380 nm to 650 nm. Most preferably, the light for illumination has a wavelength in the range from 380 nm to 500 nm.

According to one embodiment the treatment comprises an illumination time that is in the range of 1 min to 72 h, preferably in the range from 2 min to 48 h more preferably in the range from 3 min to 30 h. The illumination time of a short illumination treatment is in the range of 1 min to 1 h, preferably in the range from 2 min to 30 min, more preferably in the range from 3 min to 10 min, most preferably in the range from 4 to 6 min. The illumination time of a long illumination treatment is in the range of 1 h to 72 h, preferably in the range from 2 h to 48 h more preferably in the range from 3 h to 30 h.

According to one embodiment the radiance of the illumination light is in the range from 0.01 to 1 W/cm$^2$, preferably in the range from 0.02 to 0.9 W/cm$^2$, more preferably in the range from 0.03 to 0.7 W/cm$^2$, most preferably in the range from 0.04 to 0.6 W/m$^2$. In case of a short illumination time the radiance of the illumination light is in the range from 0.1 to 1 W/cm$^2$, preferably in the range from 0.2 to 0.9 W/cm$^2$, more preferably in the range from 0.3 to 0.7 W/cm$^2$, most preferably in the range from 0.4 to 0.6 W/m$^2$. In case of the long radiation time the radiance of the illumination light is in the range from in the range from 0.01 to 0.1 W/cm$^2$, preferably in the range from 0.02 to 0.09 W/cm$^2$, more preferably in the range from 0.03 to 0.07 W/cm$^2$, most preferably in the range from 0.04 to 0.06 W/m$^2$. In case of the long radiation time the radiance of the illumination light is in the range from 0.01 to 1 W/cm$^2$, preferably in the range from 0.02 to 0.09 W/cm$^2$, more preferably in the range from 0.03 to 0.07 W/cm$^2$, most preferably in the range from 0.04 to 0.06 W/m$^2$.

According to a one embodiment the composition comprises a photosensitizer in addition to reactivity factor and targeting factor. Photosensitizers according to the invention are light-sensitive active substances which are photochemically excited by light of appropriate wavelength and intensity and react chemically with other substances, which leads to the degradation of the substance. Preferably, this photosensitizer is a porphyrin, more preferably a porphyrin selected from porfimer sodium, psoralene, talaporfin, temoporfin, photofrin, Porphine, chlorine, bacteriochlorin, expanded porphyrin, verteporfin and phthalocyanine. Most preferably the porphyrin is verteporfin. As shown in the examples a verteporfin enhances the degradation of lipofuscin by the tested SAD.

When the compound or composition is administered directly to the eye less compound is necessary compared to an intravenous injection. The porphyrin photosensitizer may be administered at a dose per eye in mg that is less than $\frac{1}{10000}$, less than $\frac{1}{2000}$, less than $\frac{1}{1000}$, than $\frac{1}{500}$, less than $\frac{1}{250}$, less than $\frac{1}{100}$ of the calculated total body dose in mg. According to one embodiment of the second aspect the porphyrin photosensitizer is administered at a dose per eye in mg that is less than $\frac{1}{10000}$, preferably less than $\frac{1}{2000}$, more preferably less than $\frac{1}{1000}$ of the calculated total body dose in mg.

According to one embodiment of the composition for use the treatment comprises administering an intravitreal injection of the photosensitizing composition to a patient with a retinal lipofuscinopathy and a light that is different from laser light is applied.

The compounds or compositions according to the invention may in addition to the reactivity factor and targeting factor comprise a permeability factor.

Permeability factors have a lipophilic or amphiphilic character. Without being bound to theory the permeability factor may interact with the lipofuscin promoting the solubility of lipofuscin components and thus the accessibility to cellular degradation mechanisms. Moreover, the permeability factor may interact with the cellular membrane and modulate the transmission of substances through membrane, thus improving the transport of lipofuscin degradation products.

Examples of permeability factors are bile acids, polyethylenglycols (PEG), polysorbates cyclic sugars and uncouplers.

Polyethylene glycol (PEG) according to the invention includes the standard polyether compound with the general structure H—(O—CH2-CH2)n-OH but also any branched or modified PEG such as methoxy PEG. A number behind the PEG identifies the average molecular weight.

An uncoupler according to the invention is a compound which cycles across the membranes causing the dissipation of electrochemical gradient, in particular the proton gradient.

According to one embodiment the permeability factor is selected from PEG 400, Tween 80 and cyclodextrin.

The permeability factor may exhibit a lipofuscin degrading effect even without the reactivity and targeting factor (see Example 16). Thus, according to a third aspect of the invention, a compound or composition is provided, comprising at least one permeability factor for use in the treatment of lipofuscin associated diseases.

The compound or composition for use in the treatment of lipofuscin associated diseases is not cyclodextrin alone.

EXAMPLES

Example 1

Degradation of Lipofuscin is Dependent on the Reactive Chemical Species

To explore the role of the reactive chemical species the human retinal pigment epithelium (RPE) cells were treated with the super oxide anion donor (SAD) soraprazan ((7R,8R,9R)-2,3-Dimethyl-8-hydroxy-7-ethoxy-9-phenyl-7,8,9,10-tetrahydro-imidazo-[1,2-h][1,7]-naphthyridin)—a member of the THPE family—either alone or in combination with a known radical oxygen scavenger, cardioxane.

After growing the hRPE-cells to confluence, the test compounds were added to seven cell cultures and the cells were incubated at 37° C. and 5% $CO_2$. The SAD was added to the cell cultures in a concentration of 50 µg/ml either alone or in combination with cardioxane in a concentration of 10 µM, 50 µM or 100 µM. Additionally, three cell cultures were incubated only with cardioxane in a concentration of 10 µM, 50 µM or 100 µM. As control, one cell culture was grown without test compounds.

After one week of incubation micrographs of the differently incubated RPE cells were taken as shown in FIG. 2A to H. In the original images, lipofuscin in cells is visible as a yellow-gold-orange fluorescent structure, before a blue background. In the grey scale reproduction in FIG. 2 the yellow-gold-orange structure appear light grey (yellow) or dark grey (gold-orange) before a grey background. Areas of degradation of lipofuscin in the hRPE cells appears as bright blue to whitish structures which appear white in the in the grey scale reproduction and are circled in FIG. 2A.

The bright blue structures are only observed in the experimental set up with SAD alone (FIG. 2A). Thus, only the treatment with SAD alone lead to removal of lipofuscin. Cells incubated with cardioxane alone do not show any degradation of lipofuscin. Moreover, addition of cardioxane to SAD abolishes the degradation of lipofuscin that is seen with the SAD alone. Accordingly, a radical scavenger such as cardioxane prevents degradation suggesting that a radical mediated mechanism is the basis of the lipofuscin removal observed with the SAD.

Example 2

In Vitro Degradation of N-Retinylidene-N-Retinylethanolamine (A2E)

The degradation of N-retinylidene-N-retinylethanolamine (A2E)—component of lipofuscin—in an aqueous solution water was measured in the presence of potential degradation mediators and light illumination.

In a cell-free assay, A2E was dissolved in deionized $H_2O$ in a concentration of 20 µM and the solution was divided into two parts. To one part of the A2E solution verteporfin was added in an amount of 25 µM. Samples of the A2E solution with and without verteporfin were illuminated with a LED-Lamp SunaECO 1500, Tropic Marin either for 1 min at 689 nm or for 5 min with white light. Non-illuminated samples of A2E solution incubated with and without verteporfin for 5 min served as controls.

The amounts of A2E and its epoxides (A2E+O, A2E+2O) remaining were quantified by combined liquid chromatography and mass spectroscopy (LCMS) using the transitions indicated in Table 1.

TABLE 1

| Measured A2E and its epoxides | | | |
|---|---|---|---|
| Detection | A2E | A2E + O | A2E + 2O |
| Q1 (parent ion) | 592.4 | 608.3 | 624.3 |
| Q3 (product ion) | 71 | 176 | 196 |

As shown in Table 2 after illumination of the A2E for 1 min with light at 689 nm only 76% of the A2E could be detected with non-illuminated A2E. Using white light and a longer illumination time (5 min) lead to a more dramatic reduction to only 8% of the non-illuminated A2E. This result shows that A2E in solution is degraded upon illumination.

Table 2 also shows that illumination of an A2E suspension containing verteporfin leads to a stronger decrease of A2E. Thus, the photosensitizer verteporfin increases the rate with which A2E is removed or otherwise degraded.

TABLE 2

| Results of illumination of A2E alone or in the presence of verteporfin | | |
|---|---|---|
| Treatment | A2E (nM) | A2E (% control) |
| A2E non-illuminated, 5 min | 32445 | 100 |
| A2E 689 nm, 83 s * | 24605 | 76 |
| A2E white light, 5 min | 2637 | 8 |
| A2E + Verteporfin non-illuminated, 5 min | 28864 | 89 |
| A2E + Verteporfin 689 nm, 83 s * | 14338 | 44 |
| A2E + verteporfin white light, 5 min | 1295 | 4 |

Example 3

Generation of RPE Cells Including A2E

ARPE-19 cells (ca. 10.000 cells) are seeded in DMEM+10% FBS+1% P/S in 96-Well-Plates and grown at 37° C. and 0.5% $CO_2$. After one day 25 µM of A2E is added to each of the wells and the cells are left for quiescence for three days before treatment with the SADs.

Example 4

Generation of RPE Cells Including Lipofuscin 4.1 Lipofuscin Isolation

RPE cells from a human donor are suspended in an aqueous buffer and disrupted by sonication for 25 min at 4° C. using a Soniprep 150 (MSE) fitted with an exponential microprobe. The sonicated material is centrifuged at 60 g for 7 min to remove cellular debris and the resultant supernatant is centrifuged at 6000 g for 10 min to sediment the pigment granules. This sediment is resuspended in an aqueous solution of sucrose in a concentration of 0.3 M and layered onto a discontinuous sucrose gradient which consisted of eight layers of solutions with a decreasing concentration of sucrose: 2 M; 1.8 M; 1.6 M; 1.55 M; 1.5 M; 1.4 M; 1.2 M and 1 M. The overlayered gradient is centrifuged on a swing out head at 103,000 g for 1 hr. At the end of the centrifugation two distinct pigmented fractions are observed. The upper fraction being a diffuse light brown band at the interface of the layers with 1.55 and 1.6 M sucrose and the lower fraction constituting a dark brown sediment which passes even the sucrose layer with the highest concentration (2 M). Using both bright field and fluorescence microscopy the upper band is identified as lipofuscin and the lower as melanin.

The two fractions are removed from the sucrose gradient, diluted in PBSA and centrifuged at 6000 g for 10 min. Each sediment is resuspended in a 0.3 M sucrose solution and further purified on a second sucrose gradient as described above. Again the fractions are removed from the second gradient, diluted in PBSA and centrifuged at 6,000 g for 10 min. The pellet resulting from each pigmented zone is washed five times in PBSA and stored at −20' until required.

4.2 RPE Cells Feeding with Lipofuscin

ARPE-19 cells (ca. 10.000 cells) are seeded in DMEM+ 10% FBS+1% P/S in 96-Well-Plates and grown at 37° C. and 0.5% $CO_2$. After one day 300 lipofuscin granula/cell are added to the wells and the cells are grown for an additional 24 h before treatment with SADs.

Example 5

Assay Method for Donor RPE Cells

RPE cells from aged human donors contain large amounts of lipofuscin, which can be easily quantified microscopically due to its auto-fluorescence. Therefore, the aged human RPE cells mimic the pathological situation observed in patients, in which RPE cells are completely filled with lipofuscin. RPE cells from aged human donors (ca. 10.000 cells) are seeded in DMEM+10% FBS+1% P/S in 96-Well-Plates and grown at 37° C. and 5% $CO_2$. When the cells are 80% confluent, the cells are treated with SADs.

Example 6

Assay for Binding to A2E Melanin

To study the binding of A2E to melanin, a suspension of 2 mg/ml natural melanin (*S. officinalis*) is prepared in PBS, pH 7.4. The melanin suspension is brought to 37° C. and sonicated for 15 min to form a uniform suspension. The melanin suspension (0.75 ml) is measured in aliquots into glass test tubes (12×75 mm) under continuous shaking to avoid sedimentation. The solution of A2E (0.75 ml) is added to the above-mentioned melanin aliquots, and the tubes will be incubated in a shaker incubator at 37° C. and 300 rpm for 4 h.

Controls are prepared by incubating A2E in the absence of melanin in incubation medium and by incubating melanin without A2E. Compounds are added to melanin suspension from stock solutions. After incubation, the suspensions are centrifuged at 13,000 rpm for 15 min at room temperature to remove the melanin granules. The supernatant is collected, diluted with acetonitrile and analyzed by an LC-MS/MS method to determine the concentration of SAD in the supernatant. The kinetic parameters of binding study, i.e., maximal binding capacity (rmax) and the binding affinity (k) are determined for A2E according to the previously reported method (Cheruvu et al., 2008).

FIG. 3A shows the result of the binding experiment of the test compounds to the A2E complex in form of a column diagram. A high percentage of soraprazan and demethoxysoraprazan—about 46% and about 53%, respectively—are found bound to the melanin A2E particles. Also verteporfin and R/S-demethoxysoraprazan bind to the A2E melanin particles although to a lower percentage.

In a related experiment, the affinity of a SAD for metal ions is tested. The SAD is incubated at various ratios with metal ions such as Fe II or Fe III and the absorbance of light by complexes is measured. When combined in a molar ratio of soraprazan to $FeCl_3$ of 3:1, a difference spectrum suggests interaction between the species, which may explain some aspect of pigment binding. FIG. 3B shows the absorbance in dependence of the illumination wavelength for a soraprazan solution an $FeCl_3$ solution and a solution of soraprazan and $FeCl_3$. Further the graph of FIG. 3B shows a difference spectrum representing the $FeCl_3$ absorption subtracted from the soraprazan+$FeCl_3$ absorption. Comparing the difference spectrum with soraprazan spectrum it can be concluded that the combination of soraprazan+$FeCl_3$ has a higher absorption above 290 nm than the individual components.

Example 7

Melanin and Lipofuscin Increase the Cellular Uptake of Verteporfin

For testing factors influencing the cellular uptake of verteporfin to two cell types used:
ARPE-19, a human RPE cell line that lacks melanin and lipofuscin
HuRPE, RPE cells isolated from human donor eyes that contain melanin and lipofuscin The cells were treated with 200 µl of a culture medium that contained 278 nM Verteporfin for the indicated time, the culture medium was discarded, the cells trypsinized, resuspended in 500 µl medium and counted.

Table 3 shows the results of verteporfin uptake after 1 and 18 h respectively. Already after 1 h of incubation the concentration of verteporfin in HRPE is more than two-fold compared to the concentration in ARPE-19. After 18 h the concentration increased about four-fold in HuRPE cells and about two-fold in ARPE-19 cells. Thus, the difference in concentration becomes even more pronounced in the two cell lines becomes even more pronounced over time. Accordingly, the melanised HuRPE cells exhibit a higher verteporfin uptake than in non-melanised ARPE cells and the difference increases over time. This suggests an uptake rate that is constantly higher that in ARPE-19 cells.

TABLE 3

| Cellular verteporfin uptake | | | |
| --- | --- | --- | --- |
| Cell type | Incubation time (h) | Cell Number after incubation time | Verteporfin in the cells after incubation (nM) |
| HuRPE | 1 | 283.750 | 339 |
| ARPE-19 | 1 | 356.250 | 159 |
| HuRPE | 18 | 243.750 | 1206 |
| ARPE-19 | 18 | 221.250 | 351 |

Example 8

Assay for Effects of Multiple Compounds in Screen Format

The method in example 2 is adapted to a 96-well format in which 300 µL of the test suspension or solution is added to each well in the micro-titre plate. Light is provided by an LED array and diffused through a photographic filter. After illumination the plate is centrifuged in a plate centrifuge (1000 g, 1 min) and then placed in a refrigerated HPLC injector where samples are continuously injected onto an LCMS system to determine relative levels of A2E and its epoxides following illumination.

Example 9

High Throughput Flow Cytometry Assay for Detecting Lipofuscin Degradation

ARPE19 cells are incubated either with or without A2E (20 µM) for 3 days and then brought into suspension by light trpysinization. The cells are passed through a cytometer to detect yellow fluorescence. As shown in FIG. 4 upper panel cells incubated with A2E (FIG. 4 lower panel) are detected with high yellow fluorescence. This indicates a large amount of A2E. Cells incubated without A2E (FIG. 4 upper panel) have inherently low yellow fluorescence. Treatment with lipofuscin reducing drugs results in an intermediate distribution of A2E in the cells. Thus, this assay may be used to test the elimination of lipofuscin by SADs.

Example 10

Clinical Use of the Photosensitizer to Treat AMD

A patient with putative dry AMD is examined and baseline retinal fluorescence is determined using the blue laser imaging device (Heidelberg engineering). The patient is subject to an intravenous dose of 6 mg/m$^2$ verteporf in by means of infusion of 30 ml over 10 minutes. An alternative to intravenous application is the direct intravitreal application of verteporf in. In this case, ca 4 µg of verteporfin is administered to an affected single eye. Fluorescence after 1, 2 and 4 weeks is compared with fluorescence at baseline. The eyes are treated alternately.

In the standard verteporfin treatment, fifteen minutes after the start of the infusion, a laser light at 689 nm delivered 50 J/cm$^2$ by application of an intensity of 600 mW/cm$^2$ over 83 seconds using a spot size with a diameter 1000 µm. For the purposes of treatment of AMD, laser light is not necessary to promote removal of lipofuscin in the presence of a verteporfin. After administration of verteporfin to a patient an exposure of the eyes of the patient to mild indoor light of about 500 lux. Alternatively, low filtering sunglasses can be used as a means to maintain an exposure of the eyes of the patient to 500 lux when outdoors. The exposure should be maintained for a period of at least 6 h per day.

Blue light laser retinal fluorescence is measured at days 7, 14 and 28 after treatment and compared with pre-treatment values. Specific reductions of retinal fluorescence>1-20% are on post-treatment examination. In certain patients, the effect is observed in the absence of laser light treatment. The treatment is repeated with intervals of 3 month to reduce the overall levels of lipofuscin.

Example 11

Verteporfin Injection into the Vitreous of Abca4 (−/−) Mice

2 µl of a Verteporfin solution were injected into the vitreous of eyes from Abca4 (−/−) mice (12 month old) which lack the Abca4 transporter in the disk membranes of photoreceptors. Four weeks after injection the eyes of the mice were enucleated, embedded into the epoxy resin Epon™ and cut into semi-thin sections. As a control eyes of age-matched untreated mice lacking the Abca4 transporter were prepared in the same way. FIG. 5 shows electron micrographs of the semi-thin sections of both untreated (FIG. 5a) and treated mice (FIG. 5b). The RPE cell layer is marked by arrows in the Figure. Comparing the micrographs of the semi-thin section of eyes of untreated (FIG. 5a) and treated (FIG. 5b) mice the cytoplasm of the RPE cells of untreated mice appears much denser due to the targeting of confluent lipofuscin components. Thus, substantial amounts of lipofuscin and melanolipofuscin were removed from the cytoplasm of RPE cells as a result of the lipofuscin treatment. In treated eyes predominately melanin granules remained in the cytoplasm of RPE cells. This result shows that treatment with verteporfin is possible under normal daylight illumination.

Example 12

Quinolone Injection into the Vitreous of Abca4 (−/−) Mice

Various compounds are photoactive or photosensitisers and also possess lipophilic properties compatible with the partition into lipofuscin containing cells. The quinolone antibiotics are examples of such compounds. Martinez et al 1998 (Photochem Photobiol. 1998 April; 67(4):399-403. Fluoroquinolone antimicrobials: singlet oxygen, superoxide and phototoxicity. Martínez L J1, Sik R H, Chignell C F.) report that the relative photosensitiying activity of quinolones is as follows:

"fleroxacin>lomefloxacin,
    pefloxacin>>ciprofloxacin>enoxacin, norfloxacin and ofloxacin.

Studies both in vivo and in vitro have related this phototoxicity to the generation of reactive oxygen species including hydrogen peroxide and the hydroxyl radical." Based on these observations, we compared the effect of Fleroxacin (a photosensitizing quinolone) with that of Norfloxacin, an analog without this activity. Abca4 (−/−) mice (see example 11), 12 to 26 weeks old, were treated in the right eye via intravitreal injection with 2 µl of a solution containing 20 mg/ml of a solution or a suspension of the test substance. One week after injection, the eyes of the mice were enucleated, and one half of the eye was extracted by first sonication in an equal volume of saline solution, and then extraction with 3 volumes of acetonitrile. The other half of the eye was fixed with glutaraldehyde prepared as thin sections as in described in example 11. The left eye was not treated and maintained as a control. Untreated eyes of age-matched mice lacking the Abca4 transporter were an additional control.

The acetonitrile extracts were subject to analysis by HPLCMSMS using a Sciex 4000 or 4500 triple quadrupole spectrometer as is apparent in Table 1 example 2 to detect A2E and its epoxides. Using a standard curve based on authentic A2E (see example below) we computed the effective concentration of A2E in the eye tissue (not including lens and cornea). The concentration in each treated eye was then expressed as a percentage of the average concentration in all untreated eyes in the mice of the same age. The results are present in Table 4.

TABLE 4

A2E concentration in mouse eyes treated with quinolones

| Test substance | Concentration A2E (µM) in the treated eye | % of A2E relative to age matched untreated |
|---|---|---|
| Fleroxacin | 24 | 74 |
| Vehicle | 33 | 100 |
| Sparfloxacin | 36 | 99 |
| Norfloxacin | 36 | 106 |

Example 13

Tetracycline Antibiotic Injection into the Vitreous of Abca4 (−/−) Mice

Certain tetracycline analogs are known to cause photosensitivity through radical production. The relative photosensitizing effect of tetracyclines was summarized in "Hasan T Kochevar I E, McAuliffe D J, Cooperman B S, Abdulah D. Mechanism of tetracycline phototoxicity. J Invest Dermatol. 1984 September; 83(3):179-83'. These authors concluded that: "In the series demeclocycline, tetracycline, and minocycline, the efficiency of singlet oxygen generation is found to parallel the clinical observation of relative frequency of phototoxicity of these antibiotics, suggesting singlet oxygen generation as the origin of their phototoxicity."

To determine whether this relationship held for tetracyclines, we compared the efficacy of doxycycline (photosensitizer) vs. minocycline (non-photosensitizer).

Mice were treated as in example 12 with an intravitreal injection with 2 µl of a solution containing 20 mg/ml of a solution or a suspension of the test substance. One week after injection, the eyes were recovered and analysed as in examples 11 and 12. The left eye was not treated and maintained as a control. Untreated eyes of age-matched mice lacking the Abca4 transporter were an additional control. The results are presented in Table 6.

TABLE 5

A2E concentration in mouse eyes treated with tetracycline antibiotics

| Test substance | Concentration A2E (µM) in the treated eye | % of A2E relative to age matched untreated |
|---|---|---|
| Chloramphenicol | 24 | 70 |
| Doxycycline | 28 | 81 |
| Demeclocycline | 37 | 89 |
| Minocycline | 33 | 100 |
| Vehicle | 33 | 106 |

In terms of the removal of A2E from treated eyes, we observed the following at 7 days. Doxycycline (photosensitizer) had more effect than minocycline which is not a photosensitizer. Demeclocycline was notably less soluble which may explain limited effect.

Example 14

Amino Acid or Metabolite Injection into the Vitreous of Abca4 (−/−) Mice

Mice were treated as in example 12 with an intravitreal injection with 2 µl of a solution containing 40 mg/ml of a solution or a suspension of the test substance. One week after injection, the eyes were recovered and analyzed as in examples 11 and 12. The left eye was not treated and maintained as a control. Untreated eyes of age-matched mice lacking the Abca4 transporter were an additional control. The photoactive and reactive amino acids appeared to mediate reductions in A2E. Cysteine is able to interact with metals, particularly iron III (Monatshefte für Chemie/November 1991, Volume 122, Issue 11, pp 887-906) and is also redox active in the context of iron. Tryptophan is capable of absorbing and re-radiating light energy, as is riboflavin. The results are presented in Table 6.

TABLE 6

A2E concentration in mouse eyes treated with amino acids or metabolites

| Test substance | Concentration A2E (µM) in the treated eye | % of A2E relative to age matched untreated |
|---|---|---|
| Cysteine | 12 | 59 |
| Tryptophan | 13 | 66 |
| Glutathione | 35 | 89 |
| Riboflavin | 19 | 91 |
| Vehicle | 33 | 106 |

Example 15

Chelator or Metal Interactor Injection into the Vitreous of Abca4 (−/−) Mice

Mice were treated as in example 14 with an intravitreal injection with 2 µl of a solution containing 40 mg/ml of a solution or a suspension of the test substance or a concentration as indicated in the table. One week after injection, the eyes were recovered and analysed as in examples 11 and 12. The results are presented in Table 7.

TABLE 7

A2E concentration in mouse eyes treated with chelators or metal interactors

| Test substance | Concentration A2E (µM) in the treated eye | % of A2E relative to age matched untreated |
|---|---|---|
| Cysteine | 12 | 59 |
| Taurodeoxycholate EDTA | 16 | 75 |
| 1,10-phenanthroline | 20 | 91 |
| EDTA cyclodextrin | 20 | 97 |
| Vehicle | 33 | 106 |

Interaction with metals appears to have some effect or benefit for removal of A2E. However, most chelators or metal complex formers like EDTA are highly charged and unlikely to pass easily through membranes. Assisting the passage of chelators through membranes to where lipofuscin is located is likely to improve their effect, as is the use of chelators or interactors that are intrinsically lipophilic.

Example 16

Permeability Agent Injection into the Vitreous of Abca4 (−/−) Mice

Mice were treated as in example 14 with an intravitreal injection with 2 µl of a solution containing 40 mg/ml of a solution or a suspension of the test substance or a concentration as indicated in the table. One week after injection, the eyes were recovered and analysed as in examples 11 and 12. The results are presented in Table 8.

TABLE 8

A2E concentration in mouse eyes treated with permeability agents

| Test substance | Concentration A2E (μM) in the treated eye | % of A2E relative to age matched untreated |
|---|---|---|
| 20% PEG 400 | 12 | 56 |
| Cyclodextrin | 20 | 83 |
| 1% Tween 80 | 22 | 95 |
| Vehicle | 33 | 106 |

Example 17

Dye and Porphyrins Injection into the Vitreous of Abca4 (−/−) Mice

Certain dyes are photosensitisers or are capable of redox reactions. Similarly, porphoryins are in certain instances, photosensitizing. Verteporphin is one such example while pthalocyanine is less so.

Mice were treated as in example 14 with an intravitreal injection with 2 μl of a solution containing 20 mg/ml of a solution or a suspension of the test substance. One week after injection, the eyes were recovered and analysed as in examples 11 and 12.

In general, fluorescent substances were more active, suggesting that re-transmission of light energy may be relevant to the mechanism of lipofuscin removal. The results are presented in Table 9.

TABLE 9

A2E concentration in mouse eyes treated with Dyes and porhyrins

| Test substance | Concentration A2E (μM) in the treated eye | % of A2E relative to age matched untreated |
|---|---|---|
| Indocyanine green | 20 | 66 |
| Crystal violet | 23 | 71 |
| Quinine | 17 | 81 |
| Fluoroscein | 20 | 85 |
| Rose bengal | 16 | 85 |
| Phenothiazine | 27 | 85 |
| Verteporphin (2 mg/mL) | 27 | 90 |
| Indigocarmine | 22 | 98 |
| FAD | 23 | 99 |
| Phthalocyanine | 31 | 142 |

Example 18

Redox Active and Chelating Protein Injection into the Vitreous of Abca4 (−/−) Mice Mice were treated as in example 14 with an intravitreal injection with 2 μl of a solution containing 20 mg/ml of a solution or a suspension of the test substance. One week after injection, the eyes were recovered and analysed as in examples 11 and 12. The results are presented in Table 10.

TABLE 10

A2E concentration in mouse eyes treated with redox active and chelating protein

| Test substance | Concentration A2E (μM) in the treated eye | % of A2E relative to age matched untreated |
|---|---|---|
| Lactoferrin | 20 | 63 |
| Cytochrome C | 18 | 81 |
| Transferrin (apo) | 15 | 82 |

Cytochrome C shares some activity of a peroxidase and so was used here as a model peroxidase. It is an electron carrier and is redox active. Peroxidase is also active in reducing lipofuscin. Transferrin and lactoferrin are capable of binding iron with high affinity. They are also taken into cells via endocytosis. We hypothesized that they would destabilize lipofuscin through removal of iron from the aggregates.

Example 19

Redox Active Small Molecules and Chelator Injection into the Vitreous of Abca4 (−/−) Mice Mice were treated as in example 14 with an intravitreal injection with 2 μl of a solution containing 20 mg/ml of a solution or a suspension of the test substance. Unlike in previous examples where the eyes were samples after 7 days, here the eyes were taken at 16 hours after injection, the eyes were recovered and analyzed by HPLC MSMS as in examples 11 and 12. The results are presented in Table 11.

TABLE 11

A2E concentration in mouse eyes treated with Redox active small molecules and chelator

| Test substance | Concentration A2E (μM) in the treated eye | % of A2E relative to age matched untreated |
|---|---|---|
| Saline solution (0.9% NaCl) | 52 | 102 |
| Soraprazan | 31 | 61 |
| PEG-EDTA | 43 | 85 |
| Artemesinin | 38 | 75 |

These data suggest that effects may also take place in the short term.

Example 20

Calibration of HPLC MSMS Detection of A2E from Mouse Eyes

Authentic A2E was dissolved in DMSO to a concentration of 10 μM and then further diluted in water from 100 μM to 15 nM in 3-fold steps. Water solutions were diluted 1:3 with acetonitrile and then sealed in vials for injection. 6 μL of the water acetonitrile solutions were injected onto a 2×50 mm Phenyl derived HPLC column (3 μm) and eluted with a gradient from 20% acetonitrile to 100% acetonitrile over 4 minutes at a flow rate of 500 μL/minute. The masses detected and the corresponding peak areas are indicated in the following table. The relative lack of sensitivity of detection of A2E is related to the fact that A2E fragments easily to many different species of similar and low abundance. There are no main fragments that predominate the fragment spectrum.

| Standard (nM) | Peak area | | |
|---|---|---|---|
| | A2E | A2E | A2E - epoxide |
| | Molecular ion m/z+: | | |
| | 592 | 592 | 608 |
| | Fragment ion: | | |
| | 418 | 402 | 444 |
| 15 | 1430 | 479 | 259 |
| 46 | 2020 | 395 | 158 |
| 137 | 3370 | 891 | 394 |
| 412 | 10000 | 3860 | 2110 |
| 1235 | 30400 | 8060 | 4560 |
| 3704 | 130000 | 35000 | 19100 |
| 11111 | 430000 | 119000 | 81500 |
| 33333 | 996000 | 363000 | 409000 |
| 100000 | 5310000 | 1440000 | 3060000 |

The invention claimed is:

1. A method for selecting a compound suitable for treating lipofuscin-associated diseases in a patient comprising the steps of:
   a1) determining the presence of a reactivity factor in the compound by measuring the ability of the compound to generate and/or locally coordinate a radical,
   a2) determining the presence of a targeting factor in the compound by determining:
      (i) the ability of the compound to enter into a cell; and
      (ii) the ability of the compound to interact specifically with lipofuscin or components of lipofuscin, and
   b) selecting the compound that comprises the reactivity factor and the targeting factor.

2. The method as recited in claim 1, wherein the lipofuscin-associated disease is a disease of the eye or the CNS.

3. The method as recited in claim 1, wherein the reactivity factor is a radical providing agent.

4. The method as recited in claim 3, wherein the radical providing agent generates and/or locally coordinates a radical selected from hydroxyl radical (.OH), superoxide anion (O2-), oxide anion (O2-), nitric oxide (NO—), hydrogen peroxide (H2O2), and singlet oxygen (O2*).

5. The method as recited in claim 1, wherein the compound has a molecular weight below 1500 Da.

6. The method as recited in claim 1, further comprising the step of:
   a3) determining the elimination rate of lipofuscin or a lipofuscin marker from retinal epithelial cells caused by the compound comprising the reactivity factor and the targeting factor, wherein step b) further comprises additionally selecting the compound based on a predefined elimination rate threshold.

7. The method as recited in claim 6, wherein the step of determining the elimination rate of lipofuscin comprises the incubation of the compound with cells selected from retinal epithelial cells that have been incubated with the N-retinylidene-N-retinylethanolamine (A2E), retinal epithelial cells that have been incubated with animal lipofuscin, retinal epithelial cells that have been incubated with human lipofuscin, retinal epithelial cells that have been harvested from an animal, retinal epithelial cells that have been harvested from a human donor.

8. The method as recited in claim 6, wherein the lipofuscin marker is N-retinylidene-N-retinylethanolamine (A2E).

9. The method as recited in claim 1, wherein the compound is selected from one of the following classes of compounds:
   quinones, flavones, flavins, amino acids, pyroles, porphyrins, dioxetanes, photosensitizers, quinolones, quinidines, NSAIDS, psoralens, retinoic acids, and melanizing agents.

* * * * *